(12) United States Patent
Cadot et al.

(10) Patent No.: US 8,465,946 B2
(45) Date of Patent: Jun. 18, 2013

(54) EXPRESSION SYSTEM FOR THE ANTIBIOTIC-FREE PRODUCTION OF POLYPEPTIDES

(75) Inventors: Céline Cadot, Chaville (FR); Tina Ploss, Weiterstadt (DE); Ruth Schwerdtfeger, Darmstadt (DE); Bruno Winter, Stuttgart (DE)

(73) Assignee: AB Enzymes GmbH, Darmstadt (DE)

( * ) Notice: Subject to any disclaimer, the term of this patent is extended or adjusted under 35 U.S.C. 154(b) by 543 days.

(21) Appl. No.: 12/598,712

(22) PCT Filed: Feb. 12, 2008

(86) PCT No.: PCT/EP2008/001977
§ 371 (c)(1),
(2), (4) Date: Apr. 15, 2010

(87) PCT Pub. No.: WO2008/135113
PCT Pub. Date: Nov. 13, 2008

(65) Prior Publication Data
US 2010/0248306 A1    Sep. 30, 2010

(30) Foreign Application Priority Data
May 4, 2007 (DE) .......................... 10 2007 021 001

(51) Int. Cl.
*C12P 21/06* (2006.01)
*C12N 1/20* (2006.01)

(52) U.S. Cl.
USPC .................. 435/69.1; 435/252.31; 435/252.3; 435/252.32

(58) Field of Classification Search
None
See application file for complete search history.

(56) References Cited

U.S. PATENT DOCUMENTS
4,873,192 A    10/1989    Kunkel

FOREIGN PATENT DOCUMENTS

| EP | 0 185 512 A1 | 6/1986 |
|---|---|---|
| EP | 0 185 512 B1 | 6/1986 |
| EP | 0 284 126 A1 | 9/1988 |
| EP | 0 284 126 B1 | 9/1988 |
| EP | 0 585 617 A2 | 3/1994 |
| EP | 0 585 617 B1 | 3/1994 |
| WO | WO-96/23073 A1 | 8/1996 |
| WO | WO-01/90393 A1 | 11/2001 |
| WO | WO-2004/078953 A1 | 9/2004 |
| WO | WO-2005-061716 A2 | 7/2005 |

OTHER PUBLICATIONS

Stratagene (phagemid vector map of pBluescript KSII, retrieved from the Internet <http://bio.classes.ucsc.edu/bio20L/info/content/molbio2/pbluescript_2_ks.pdf>, retrieved on Mar. 18, 2013).*

H.R. Morbidoni et al., "Synthesis of sn—Glycerol 3-Phosphate, a Key Precursor of Membrane Lipids, in *Bacillus subtilis*", *Journal of Bacteriology*, 177(20), pp. 5899-5905 (1995).

P. Hagg et al., "A host/plasmid system that is not dependent on antibiotics and antibiotic resistance genes for stable plasmid maintenance in *Escherichia coli*", *Journal of Biotechnology*, vol. 111, pp. 17-30 (2004).

X.H. Chen et al., "Comparative analysis of the complete genome sequence of the plant growth-promoting bacterium *Bacillus amyloliquefaciens* FZB42", *Nature Biotechnology*, 25(9), pp. 1007-1014 (2007).

S. Bron et al., "Segregational Instability of pUB110-Derived Recombinant Plasmids in *Bacillus subtillis*", *Plasmid*, vol. 14, pp. 235-244 (1985).

M. Herrero et al., "Transposon Vectors Containing Non-Antibiotic Resistance Selection Markers for Cloning and Stable Chromosomal Insertion of Foreign Genes in Gram-Negative Bacteria", *Journal of Bacteriology*, 172(11), pp. 6557-6567 (1990).

E. Zyprian et al., "Characterization of Signals Promoting Gene Expression on the *Staphylococcus aureus* Plasmid pUB110 and Development of a Gram-Positive Expression Vector System", *DNA*, 5(3), pp. 219-225 (1986).

J. Stulke et al., "Regulation of Carbon Catabolism in *Bacillus* Species ", *Annu. Rev. Microbiol.*, vol. 54, pp. 849-880 (2000).

G.R. Ostroff et al., Molecular Cloning with Bifunctional Plasmid Vectors in *Bacillus subtilis*, *Mol. Gen. Genet.*, vol. 193, pp. 299-305 (1984).

F.K. Khasanov et al., "Homologous Recombination Between Plasmid and Chromosomal DNA in *Bacillus subtilis* Requires Approximately 70 bp of Homology", *Mol. Gen. Genet.*, vol. 234, pp. 494-497 (1992).

J. Vehmaanpera et al., "Genetic Manipulation of *Bacillus amyloliquefaciens*", *Journal of Biotechnology*, vol. 19, pp. 221-240 (1991).

Extract from the Register of European Patents, EP 0 251 579 A1, Enterovax Research Pty. Ltd., Jan. 7, 1988.

DD 277467 A1, (withdrawn application), Dec. 1, 1988.

* cited by examiner

*Primary Examiner* — Suzanne M Noakes
*Assistant Examiner* — Jae W Lee
(74) *Attorney, Agent, or Firm* — Edwards Wildman Palmer LLP; Peter F. Corless; Christine C. O'Day

(57) ABSTRACT

The present invention relates to a microbial expression system for the production of polypeptides based on the use of extrachromosomal DNA, whereby no antibiotic marker genes for the selection of the host cell but DNA sequences that encode glycerine-3-phosphate dehydrogenase are used, and, thus, the production of the desired polypeptide, e.g., xylanase, does not need the addition of antibiotics. The expression system is free from antibiotic-resistance genes. The invention further relates to a DNA sequence that encodes a polypeptide with glycerine-3-phosphate dehydrogenase activity as well as a polypeptide with glycerine-3-phosphate dehydrogenase activity.

13 Claims, 17 Drawing Sheets

Fig. 1

Figure 4:
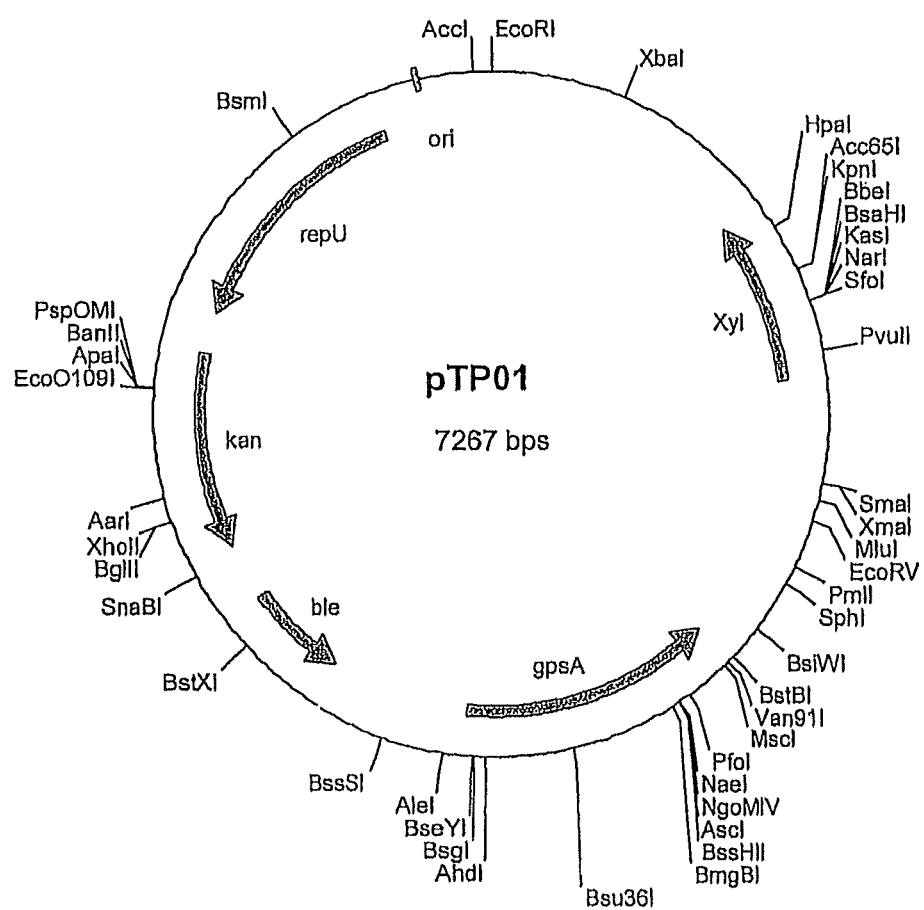

```
   1  aagggtacta  tgggtaaacc  tgtcgtagcc  attgtcggaa  gaccgaatgt
  51  gggaaaatcc  acaatcttta  accggattgc  gggtgaaaga  atttcaatag
 101  tagaagatac  ccccggagtg  acgcgggacc  ggatatacag  ttcggcggaa
 151  tggctgaatt  atgattttaa  cctgattgat  acgggcggaa  ttgatatcgg
 201  agacgagccg  tttctgacac  agatccgcca  gcaggctgaa  atcgccatgg
 251  acgaggctga  tgtgatcatc  tttatggtga  acggccgcga  aggtgtgacg
 301  tctgcggatg  aagaagtggc  aaaaatactg  taccggacga  aaaaaccggt
 351  cgtattagcc  gttaataaat  tagataatac  cgaaatgaga  gcgaacattt
 401  atgactttta  tgcgctcggc  tttggagaac  cgtatccgat  ttcggggaca
 451  cacggtttag  gattgggaga  tttgctcgat  gcttgtgccg  agcattttaa
 501  aaacattccg  gagacgaagt  acagtgatga  tgtcgttcaa  ttctgcctga
 551  tcggccgccc  gaatgtcgga  aaatcatccc  ttgtcaatgc  gatgctcggc
 601  gaagagcggg  ttatcgtgag  caacgtagcc  ggaacgacta  gagacgctgt
 651  ggatacggcg  ttcacttaca  atcagcagga  atttgtaatc  gttgacacgg
 701  cgggaatgag  aaaaaagggt  aaagtatatg  aaacaacaga  aaaatacagt
 751  gtgctgcggg  cgttaaaagc  cattgaccgc  tcagacgtcg  tcggcgttgt
 801  gctgaatgca  gaagaaggca  tccttgagca  ggacaagcgg  atcgccggat
 851  acgcccatga  agccgggaaa  gccgtcgtca  ttatcgtaaa  caaatgggat
 901  gccgttgata  aggacgagcg  cacgatgaaa  gaatttgaac  agaatattcg
 951  ggagcatttc  caatttctcg  attatgcgcc  ggtgctgttt  atgtcggcac
1001  tgacgacaaa  gcggattcat  acactcatgc  ctgcgattat  taaagcgagt
1051  gaaaaccact  ctctccgcgt  gcagacaaat  atcttaaatg  atgtcatcat
1101  ggatgcggtc  gccatgaatc  cgactccgac  gcacaacggc  tcccgtctga
1151  aaatttatta  tgcgactcaa  gtcgctgtta  agccgccgag  cttcgttgtt
1201  tttgtcaacg  atccggaact  gatgcatttt  tcttatgaac  gcttttttaga
1251  aaaccgaatc  cgggacgctt  tcggatttga  aggtacgcca  attaaaatat
1301  ttgcaagagc  aagaaaataa  aaaggtgtga  tacagagatg  aaaaaagtgg
1351  caatgcttgg  agcgggaagc  tggggcactg  cactttcttt  agtgctggct
1401  gataacggac  atcaagtcat  gatgtgggga  caccgtgccg  aattgatcga
1451  tcaaatcaac  gaactgcatg  aaaacaaaga  ttacctgccg  ggtgtggagc
1501  tatcaagttc  tatcatcggg  acagccgatt  taagcgaggc  tttaaaagga
1551  gctgacttca  tcattgtggc  agtaccgaca  aaagccattc  gggaagtgct
1601  gaaaaaggct  ctgccgtaca  tcccgaaaca  atcgattttt  gttcatgtca
1651  gcaagggaat  tgagccggat  tcgcttctcc  gcatttcaga  attaatggag
1701  gaggagctgc  ctgaggagta  cagaaaagac  atcgtcgtgc  tttcagggcc
1751  gagccacgct  gaggaagtcg  gattaagaca  cccgacgact  gttacatcat
1801  cttcaaaaaa  tatcaaggct  gcagaagcgg  ttcaggattt  attcatgaac
1851  cagcatttcc  gcgtctatac  aaatcccgat  atgatcggtg  ttgaaatagg
1901  gggagcgtta  aaaaatatca  tcgctcttgc  agcggggatt  acagacggat
1951  tgggatacgg  agataatgca  aaagcggcct  taatcacccg  aggtcttgct
2001  gaaatcgcca  gactcggcac  aaagatgggc  ggaaatccgc  tcaccttttc
2051  cggcctgacc  ggcgtaggcg  atttaatcgt  gacgtgtaca  agcgttcatt
2101  cccgaaactg  gcgcgccggc  aacctgctcg  gcaaaggata  taagctggaa
2151  gctgtcctgg  ataagatggg  gatggttgtt  gaaggcgtgc  ggacgacgaa
2201  agctgcgtat  cagctgtctc  aaaaatatca  ggtgaaaatg  ccgatcacag
```

```
2251  aagcgcttca ccaagtatta tttaatgggc agaaggtaga aactgccgta
2301  gaatccttaa tggccagagt gaaaacccat gagatggaag acttggtcaa
2351  cacattcgaa aaccgggtga agtga caata acatgccgtc agcatattct
2401  gaagtgacga aagtacaaaa cgcagaactc tccggctgaa atcgcttaaa
2451  acatttgctg atttaggcag aagaggatgc agacgtacgc atctacgcat
2501  actatagcat cgaagtccaa gagagtgtat ctcagacgta caggtgaata
2551  tagtcaactt gactgaagca aagtccccct ctttgcttca gttttttttgt
2601  tttttcaata gatggaaaac ctgttgatct tttcaacatt tgtatattaa
2651  aatgaaatat aacgcttaca atgatgggac gggggggcacg aacgtgagtg
2701  tggcattgat gaaaatgtgg tttgcgcttg gtgctatggg attaatgttt
2751  gttgcggtcg cctctattta tgtcagcagg tacaaagtga aaacaaact
2801  gataaaagca gcggtttctt cactcgctta tgcctgcatg gtcatctcgg
2851  gattgatcgt gttaatggtc gttttcagcg ggcctgtcaa tgaataaagc
2901  caaaggggg cgcggaatgc ataagttaaa aatggccgtc ataacggcaa
2951  tggcggtgct tctgctgtcg ggctgtctgt accctgaagc aaaaaaaact
3001  gaaaataaag tatcttacaa acatcagctt cagcaggtgc aagcggcagt
3051  ggatgaattt aaaaaggcga acggcggact tctgccgatt cagacaaaag
3101  atatgaaaac accgctctat caaaaatatc cgatagattt taagcggctc
3151  gcgcccagat acatcgagga gccgccggcc tcagcttatg aaagcggagg
3201  aatgtaccaa tacgtgcttg tcgatgtgga aaataagccg accgtcaagc
3251  tggtcgatct ccaaatggcg gaagcaatcc gcgacatgaa gctgcgtgtc
3301  aaaatgtatc aggaaaagca tacatatcct ccctatgagg acgctgtttc
3351  aaaagggctg ttcactttaa ataaaaaaaa gctcggcatg aaagactctc
3401  cttcagtcaa aagtccggtt tcaggcacgt ctctgccgct tttaatcggc
3451  gctgacggag aaatctatgc cgactatcgc gtcgatctcg cccgctgcct
3501  gaaggaaaac aaaaagaaaa tcaaaccggg ggcggaaatt caggatattt
3551  tatggaaaga gactcctttc gtcccggcct tttcagtcac atacaccgta
3601  aatgaaaaac aggaacccgt ttttttagaa agtcaaacga aacaggaatg
3651  aaccttttc ccgcgcatac aaatagggag aaaggttttt ttgattttga
3701  tagaaaagac tgcct
```

Fig. 2

```
  1  MKKVAMLGAG  SWGTALSLVL  ADNGHQVMMW  GHRAELIDQI
 41  NELHENKDYL  PGVELSSSII  GTADLSEALK  GADFIIVAVP
 81  TKAIREVLKK  ALPYIPKQSI  FVHVSKGIEP  DSLLRISELM
121  EEELPEEYRK  DIVVLSGPSH  AEEVGLRHPT  TVTSSSKNIK
161  AAEAVQDLFM  NQHFRVYTNP  DMIGVEIGGA  LKNIIALAAG
201  ITDGLGYGDN  AKAALITRGL  AEIARLGTKM  GGNPLTFSGL
241  TGVGDLIVTC  TSVHSRNWRA  GNLLGKGYKL  EAVLDKMGMV
281  VEGVRTTKAA  YQLSQKYQVK  MPITEALHQV  LFNGQKVETA
321  VESLMARVKT  HEMEDLVNTF  ENRVK
```

Fig. 3

```
              10         20         30         40         50         60         70         80
               *          *          *          *          *          *          *          *
B. amyloliq.  aagggtactatggggtaaacctgtctgtcgtagccattgtcggaagaccgaatgtgggaaatccacaatctttaaccggattgc
B. subtilis.  ..........................................g......a.......................a........
B. lichenif.  ..............a...........................a..t....c......g..g...g.......a..c......

90        100        110        120        130        140        150        160
               *          *          *          *          *          *          *          *
B. amyloliq.  gggtgaaagaatttcaatagtagaagatacccccggagtgacgcggatatacagttcggcggaatggctgaatt
B. subtilis.  ...a........................................t..c......aa....t...........c..t..............
B. lichenif.  ...c......g..t..g........a..t..c...............t.................c..t..c..g...........c 170        180        190        200        210        220        230        240
               *          *          *          *          *          *          *          *
B. amyloliq.  atgatttaacctgattgatacgggcggaattgatatcggagagacgagccgtttctgacacagatccgccagcaggctgaa
B. subtilis.  ........tt...........................t....t..t......t.ag.g....t.............a........
B. lichenif.  .c..c..c........................a........c..ag...c..t..t..g..g......t.....t.....c..g 250        260        270        280        290        300        310        320
               *          *          *          *          *          *          *          *
B. amyloliq.  atcgccatgacgaggctgatgtgatcatctttatggtgaacggccgaaggtgtgacgtctgcggatgaagaagtggc
B. subtilis.  ........t..a.g..c....t..t........t.t............t......c......ag...t.............
B. lichenif.  ........a..a..........ac.........t..t..c...ac........c..c..ag.c..t...............
```

Fig. 3 (continuation 1)

```
             330       340       350       360       370       380       390       400
              *         *         *         *         *         *         *         *
B. amyloliq. aaaatactgtaccggacgaaaaaaccggtcgtattagccgttaataattagataataccgaaatgagagcgaacattt
B. subtilis  g......tt.....c..a.....g..t..t..t.....g........c.g....c..a...........t........
B. lichenif. ........tt.a......t..a......c.......tc.g..g......g.g......c.t..........a.......

410       420       430       440       450       460       470       480
              *         *         *         *         *         *         *         *
B. amyloliq. atgactttatgcgctcggctttggagaaccgtatccgatttcggggacacacggtttaggattgggagattgctcgat
B. subtilis  ....t..........t..a........c..g.......a........ac.c....c....t.....a..g...
B. lichenif. .c..t..............c........c...g.......tc..........a.......g..t..cc.t..tc.c....c......t..c 490       500       510       520       530       540       550       560
              *         *         *         *         *         *         *         *
B. amyloliq. gcttgtgccgagcattttaaaaacattccggagacgaagtacagtgatgatgtcgttcaattctgcctgatcggccgcc
B. subtilis  ..cgt...a..................t..a.....a..a..a..ta.............t........a..t..
B. lichenif. ..ggtcag...a...............tgag.....a..........................c........g..

570       580       590       600       610       620       630       640
              *         *         *         *         *         *         *         *
B. amyloliq. gaatgtcggaaatcatcccttgtcaatgcgatgctcggcgaagagcgggttatcgtgagcaacgtagccggaacgacta
B. subtilis  a.........................g...........a.........a.c....t.c........g..t.......a.
B. lichenif. .c.......................a.c......a.t..a........c..............c........ta.t..g......gc 650       660       670       680       690       700       710       720
              *         *         *         *         *         *         *         *
B. amyloliq. gagacgctgtggatacggcgttcacttacaatcagcaggaatttgtaatcgttgacacggcgcggaatgagaaaaaggt
B. subtilis  .l....t....t.....t.a..t.......c.........g......c.t..t.a..t....c.........a..g
B. lichenif. .c......ca.t..c.....ag...t..a........aaga..c........c.....g..t..a..c..g........g
```

Fig. 3 (continuation 2)

```
              730       740       750       760       770       780       790       800
               *         *         *         *         *         *         *         *
B. amyloliq. aaagtatatgaacaacagaaaaatacagtgtgctgcgggcgttaaaagccattgaccgctcagacgtcgtcggcgttgt
B. subtilis  .....c....g..t.g..g..t.....a....c....g.............a......g.cg......
B. lichenif. ......g....gg......t.............c..c..c..a...t....g..g..c......a........t....c...

810       820       830       840       850       860       870       880
               *         *         *         *         *         *         *         *
B. amyloliq. gctgaatgcagaagaaggcatccttgagcaggacaagcggatcgccggatacgcccgatgaagccgggaaagccgtcgtca
B. subtilis  ...g...gc...........ta......a..............t...t.t..a.c....g..c..g............
B. lichenif. ct..g.c.gc...........ta.........................t....c..t.g......a..a.....t..t....

890       900       910       920       930       940       950       960
               *         *         *         *         *         *         *         *
B. amyloliq. ttatcgtaaacaaatgggatgccgttgataaggacgagcgcacgatgaaagaatttgaacagaatattcgggagcattc
B. subtilis  ..cg...............t....c..a..t..a...............g.a......c..t.....t
B. lichenif. .cg..................a..c..a..a.......g............g.a..gg..a.a..c..c..t 970       980       990       1000      1010      1020      1030      1040
               *         *         *         *         *         *         *         *
B. amyloliq. daatttctcgattatgccgggtgctgttatgtcggcactgacgacaaagcggattcatacactcatgcctgcgattat
B. subtilis  ........g...........aa.c..a......t.ct.a...a....a......c....t.g...........
B. lichenif. ......t.g..c..c......t..tt......c..tt...t.a.....c..c......g..g.........g.c..

1050      1060      1070      1080      1090      1100      1110      1120
               *         *         *         *         *         *         *         *
B. amyloliq. taaagcgagtgaaaaccactctccgcgtgcagacaaatatcttaaatgatgtcatcatggatgcggtcgccatgaatc
B. subtilis  c...t.............t..t.a..t..a......cg...........................c..t.g..a.....
B. lichenif. g.cg......c.......t..ga.ga.g........c.......tc.t......a......t...........g..t......c..
```

Fig. 3 (continuation 3)

```
                   1130      1140      1150      1160      1170      1180      1190      1200
                     *         *         *         *         *         *         *         *
B. amyloliq.   cgactccgacgcacaacggctcccgtctgaaaattattatgcgactcaagtcgctgttaagccgccgagcttcgttgtt
B. subtilis    .....a......t..t..t...c.............gt.g..a......a.....g
B. lichenif.   ........g.......t..t..aaa...gt.a........a..........g............ca..t..c...a 1210      1220      1230      1240      1250      1260      1270      1280
                     *         *         *         *         *         *         *         *
B. amyloliq.   tttgtcaacgatccggaactgatgcatttttctttagaaaccgcttttcttagaaaccgaatccgggacgctttcggatttga
B. subtilis    .......a..........a..c..g.....................a.a.....g......t......
B. lichenif.   ........t..c..t..g..........c...........g........g..a..c.......c........

1290      1300      1310      1320      1330      1340      1350      1360
                     *         *         *         *         *         *         *         *
B. amyloliq.   aggtacgccaattaaaatatttgcaagagagcaagaaaataaaaggtgtgatacagagatgaaaaagtgcaatgcttgg
B. subtilis    g..g..a...c..............t.............at..a.c........ca..
B. lichenif.   ...a..a......c.gg..t..c.........g......ag.--.a..a....c......at.g..tt.g..

1370      1380      1390      1400      1410      1420      1430      1440
                     *         *         *         *         *         *         *         *
B. amyloliq.   agcgggaagctgggggcactgcactttctcttagtgctgctgataacggacatcaagtcatgatgtggggacaccgtgccg
B. subtilis    .....g..t.....a..a....gg....t..aa.......t..a..g...gtgtg........ct.......a.
B. lichenif.   ...c...........a..a...ct.gg..gc.c..tt...g..c...cagt.cg..t..gtgc..a....t....aa.

1450      1460      1470      1480      1490      1500      1510      1520
                     *         *         *         *         *         *         *         *
B. amyloliq.   aattgatcgatcaaatcaacgaactgcatgaaaacaaagattacctgccgggtgtggagctatcaagttctatcatcggg
B. subtilis    .t..a..tc......t..t..gt.....at.............tt......aa...ta....g..t.ca..c..t.aa..a
B. lichenif.   ..c......tc.g......t....................t..........ca.a..t..tgaaaacg.gcgt.cc
```

Fig. 3 (continuation 4)

```
                  1530      1540      1550      1560      1570      1580      1590      1600
                     *         *         *         *         *         *         *         *
B. amyloliq. acagccgattaagcgaggcttaaaaggagctgactcatcattgtggcagtaccgacaaaagccattcgggaagtgct
B. subtilis  ...a...a.g.aa.......g.ttc..ac..a..tg....t.c..t..g..c........a...............
B. lichenif. l...a...c.tgaa.ct..ag.ggct.at.tca.gacg............c..c...t........g..c..c....tt.

1610      1620      1630      1640      1650      1660      1670      1680
                     *         *         *         *         *         *         *         *
B. amyloliq. gaaaaggctctgccgtacatcccgaaacaatcgattttttgttcatgtcagcaaggaattgagccggattcgcttctcc
B. subtilis  ..g.c......g.c...t.tt..aa.....a.gg.ag..c..................t.........a......g..
B. lichenif. .gc.c.....g..tt.c.t...aacc..a.gg.......a.......ttca..a..........t..ca.a..g..t.

1690      1700      1710      1720      1730      1740      1750      1760
                     *         *         *         *         *         *         *         *
B. amyloliq. gcatttcagaattaatgaggagctgcctgaggagtacagaaagacatcgtcgtgctttcaggcgccgagccacgct
B. subtilis  .......t...a.t.....aatt....c..gagt..tgt........t....t..c....c..c.......t..t..g
B. lichenif. .a.....t...a.g...a.a..aa.t..g.ct..a.ta..gg.g....a.ta..........t..g..c.a....t..g 1770      1780      1790      1800      1810      1820      1830
                     *         *         *         *         *         *         *
B. amyloliq. gaggaagtcggattaagacacccgacgactgttacatcatcttcaaaaatatcaagg---ctgcagaagcggttcagga
B. subtilis  ..a.......a....gc.gc.g.....c..a........tg........g.gc.g.g...---.a.......a...g....
B. lichenif. ..a.......t....a.g...a..t......g..c.g.c.gc.g..tt.aat.g...cc.g...a.c.......

1840      1850      1860      1870      1880      1890      1900      1910
                     *         *         *         *         *         *         *         *
B. amyloliq. tttattcatgaaccagcattccgctctatacaaatcccgatatgatcggtgttgaaataggggagcgttaaaaata
B. subtilis  .c...t..t.t..ca.....t..g...c.......t.c..t....a........c.a..g..t............
B. lichenif. ..a.g..t....a.......a.........g............c..a..g..c..c...c..g......cg
```

Fig. 3 (continuation 5)

```
              1920      1930      1940      1950      1960      1970      1980      1990
                 *         *         *         *         *         *         *         *
B. amyloliq.  tcatcgctcttgcagcggggattacagagacggattgggatacggagataatgcaaaagcggcccttaatcacccgaggtctt
B. subtilis   .t..t..c....t..a..a.........t..t..a..g....t..c.......c......t..t..g..t..a..c..a...
B. lichenif.  ....t..g....c......c.........t..................g......c..gc.g..t..aa.g..ct.g 2000      2010      2020      2030      2040      2050      2060      2070
                 *         *         *         *         *         *         *         *
B. amyloliq.  gctgaaatcgccagactcggcacaaagatgggcggaaatccgctcacctttccggcctgaccggcgtaggcgatttaat
B. subtilis   ..c.........g.......a..g..a.........a...............ct.g..g..c..t..at....a..a........c.g..
B. lichenif.  ..a......c.g.........................................g..a..c..g..t..t..aa.c..g...c..g..

2080      2090      2100      2110      2120      2130      2140      2150
                 *         *         *         *         *         *         *         *
B. amyloliq.  cgtgacgtgtacaagcgttcattcccgaaactggccgccggcaacctgctcggcaaaggatataagctggaagctgtcc
B. subtilis   t..........c.....t.........a.........tt.......a......g..c......t..a...t.
B. lichenif.  ...c..c......c.........a.........ta....g..t......c.tc..........t.aa..t.

2160      2170      2180      2190      2200      2210      2220      2230
                 *         *         *         *         *         *         *         *
B. amyloliq.  tggataagatggggatggtgttgttgaaggcgtgccggacgacgaaagctgcgtatcagctgtctcaaaatatcaggtgaaa
B. subtilis   .t..ag....a...........a.c......c..c......g..t.................t..ga.g....g.t..t...
B. lichenif.  ....ag.a........c..c..........c.........a..c..t...................t..aa.g....t.g.t..a...

|2240     2250      2260      2270      2280      2290      2300      2310
                 *         *         *         *         *         *         *         *
B. amyloliq.  atgccgatcacagaagcgcttcaccaagtattatttaatggcagaaggtagaaactgccgtagaatccttaatggccag
B. subtilis   ............t.....t..c..t..g..cc....c..a..a..g....c..t..t.....t...........g..
B. lichenif.  .............c......a.........g..c..cg..a..t..g..a..c.....a..g.....a...
```

Fig. 3 (continuation 6)

```
              2320       2330       2340       2350       2360       2370       2380       2390
                 *          *          *          *          *          *          *          *
B. amyloliq.  agtgaaacccatgagatggaagacttggtcaacacattcgaaaaccgggtgaagtga------caataacatgccgtca
B. subtilis   ..g:........c.......g..t....a..t.g..t......a.aagtgt....c.a...gt.aat
B. lichenif.  ...c........a..c.............tc.t..g........t.aaa........a...-----...gcc..a...

2400       2410       2420       2430       2440       2450       2460
                 *          *          *          *          *          *          *
B. amyloliq.  -gcatattctgaagtgacgaaagtacaaaacgcagaa------ctctccggctgaaatcgcttaaaacattt-gctgattt
B. subtilis   c.......ct.a.ttga......cc.g...aa.....gaaca.c:aagtct..gg...t.c.g.......t..c.......
B. lichenif.  -t..ac.g.............--------tt..t.ctctc.tct.-----agt..gttt.a...aaa.ca...cat...-ga...c...

2470       2480       2490       2500       2510       2520       2530       2540
                 *          *          *          *          *          *          *          *
B. amyloliq.  aggcagaagaggatgcagacgtacgcatctacgcatactagcatcgaagtccaagagag-tgtatctcagacgtacag
B. subtilis   .....at.........tct...t..caagt..................---..t..a...g...
B. lichenif.  .......ag...a..ttt..c..a.gactt.....aa....a........tgga....c............t.c..aa..tgg.

2550       2560       2570       2580       2590       2600
                 *          *          *          *          *          *
B. amyloliq.  gtgaatat-----agtcaacttgactgaagcaaag-tccccctcttgcttcagtttttgtt--------tttt
B. subtilis   ..........-----.......g.........g....g........................---------c.a.
B. lichenif.  t.at...gtcac.a...tta..c........----c...........gc.....t..gcggcttttccg...c 2610       2620       2630       2640       2650       2660       2670
                 *          *          *          *          *          *          *
B. amyloliq.  caatagatggaaaacctg-ttgatcttttcaacatttgtatattaaaatgaaatataacgcttacaatgatgg-----
B. subtilis   ...g........t...g........cggcgc.........at..............t.tcttaca-----
B. lichenif.  g..atat......g..-.....a...c.ggttt..ct...-........tcacaa..aaaggt
```

Fig. 3 (continuation 7)

```
                 2680       2690       2700       2710       2720       2730       2740       2750
                   *          *          *          *          *          *          *          *
B. amyloliq.  -gacgggggcacgaacgtgagtg----tggcattgatgaaaatgtgtttgccttggtgctatgggattaatgttgt
B. subtilis   -t.tc....agg..c.....c.t..aatc.................t.a..gt.c......tc.g.......c.
B. lichenif.  a....a...a....ttc..t....a..-----.c.gtc..t.a..........ct.g..at.a......cc.g......ct.

2760       2770       2780       2790       2800       2810       2820       2830
                   *          *          *          *          *          *          *          *
B. amyloliq.  tgcggtcgcctctatttatgtcagcaggtacaaagtgaaaacaaactgataaaagcagcggtttcttcactcgcttatg
B. subtilis   g..t..a.t.c...t.a...c.c.tt..gtgcc....cgtt.tt.g..gatt...a....a...t....a..ca
B. lichenif.  a.....gattg.c..a....ca........t..t......cgtt.tt....attatcacg..g.ttg....c..ca 2840       2850       2860       2870       2880       2890       2900
                   *          *          *          *          *          *          *
B. amyloliq.  cctgcatgtcatctcggattgatcgtgttaatggtcgtttcagcggcctgtcaatgaataagcc----aaaaggggg
B. subtilis   tg..t...c....a..t..t....tg.c..g.....t....c.............tgt-.......aa
B. lichenif.  .a..t....c..........c..cg........c..tt.t......c.......c.......t..ataa.......aa 2920       2930       2940       2950       2960       2970       2980
                           *          *          *          *          *          *          *
B. amyloliq.  gcgcggaatgcataagttaaaaatggccgtcataacggcaatggcggtgcttctgctgtcggcgtgtctgtaccc----tg
B. subtilis   .t..t...gg...ac.g..gtgc..aa....tttt..-----..a..cg.gt.tt..a..c..a...t.a....t..aaa..
B. lichenif.  .attcat...a.a.tcg....cg.tctgc..gct.tttt.t..a.c.caa.ca..t.aagc.t....t.......----..

2990       3000       3010       3020       3030       3040       3050       3060
                   *          *          *          *          *          *          *          *
B. amyloliq.  aagcaaaaaaactgaaaataagtatcttacaaacatcagcttcagcaggtgcaagcggcagtggatgaatttaaaaag
B. subtilis   ..cgg....gc.g..tgc..gcca.tc...tc...g.c.....aa.....t..t.t..t........c.....
B. lichenif.  ...a..g...gg..ga....c.gc.c..c.gc.tc.g..c.....ca.ag.a.....g......t........c.ggg..
```

Fig. 3 (continuation 8)

```
                 3070      3080      3090      3100      3110      3120      3130      3140
                    *         *         *         *         *         *         *         *
B. amyloliq.  gcgaacggcggacttctgccgattcagacaaagatatgaaaacaccgctctatcaaaatatccgatagatttaagcg
B. subtilis   ..a..t..a.g..g..t..t.....a..c........tcg........a................c.....c.....c..
B. lichenif.  ....cg..a..g..............a.........gg......ggcgtg..aa..............c..t..c......ca.

3150      3160      3170      3180      3190      3200      3210      3220
                    *         *         *         *         *         *         *         *
B. amyloliq.  gctcgcgcccagatacatcgaggagccgcgcctcagcttatgaaagcggaggaatgtaccaatacgtgcttgtcgatg
B. subtilis   .t.a.........a........a.ct..a..t..aagta.g..a.t......g...gac..t..........t..c...
B. lichenif.  ...gt.c..c.g..t..g.ct...........g.a..t.c......a...c...ga....ttg.....t..........

3230      3240      3250      3260      3270      3280      3290      3300
                    *         *         *         *         *         *         *         *
B. amyloliq.  tggaaataagccgaccgtcaagctgtcgatctccaaatggcggaagcaatccgcgacatgaagctgcgtgtcaaaatg
B. subtilis   .a..g..cg.t.....t..t..at.aa.t......aa.g.....a....aa..t....tg....at...ca..c.....
B. lichenif.  ........a.........g........ca..t..g.aa......t......atg..a.g..gt.a...t..g....g.....

3310      3320      3330      3340      3350      3360      3370      3380
                    *         *         *         *         *         *         *         *
B. amyloliq.  tatcaggaaaagcatacatatcctccctatgaggacgctgttcaaaagggctgttcactttaaataaaaaagctcgg
B. subtilis   ...gtc.gg......ca......g..t..ca...t..tgc.a...tcgt.att.a..t..ac.cg..g.g....t...
B. lichenif.  ....a..tc.....c.ag......g....g....a.aa.a.tc..a..c..gaact.a....tgc.tg.cc.tg.....

3390      3400      3410      3420      3430      3440      3450      3460
                    *         *         *         *         *         *         *         *
B. amyloliq.  catgaagagactctccttcagtcaaaagtccggtttcaggcacgtctctgccgcttttaatcggcgctgacggagaaatct
B. subtilis   ggatggcag....t.a...g.c..c..aa.c......g.at..ct..........a.g..t.a..ga..........a..
B. lichenif.  ac........gg.g.....t.........cg.........c..g......c...g....c.cg....at.aaa.a...c...c..ta
```

Fig. 3 (continuation 9)

```
              3470       3480       3490       3500       3510       3520       3530       3540
                *          *          *          *          *          *          *          *
B. amyloliq.  atgccgactatcgcgtcgatctcgcccgctgcctgaaggaaataaagaaaatcaaacaaaaatcaaacaaaaatcaaacaaaaacgggggcggaaattcaggat
B. subtilis   ......t..c..gact..g..g..ttct....c..aa...g......a.cgt.t....c...a.t.....c......
B. lichenif.  .a.tg..t..c..ga.g...t.g....aagctga.....a.gtcg.....a.cgg.a..g.....c.a....g.c..a...

3550       3560       3570       3580       3590       3600       3610       3620
                *          *          *          *          *          *          *          *
B. amyloliq.  attttatggaaagagactccttcgtcccggccttttcagtcacatacaccgtaaatgaaaaacaggaacccgttttttt
B. subtilis   ..ga.t..c.t..a..c.c..t....c...g.....t..a.a...t.g.....c.........t............
B. lichenif.  t.ga.g..g......g...........t......g.....g..a.ag.....a..g.....c..............c..

3630       3640       3650       3660       3670       3680       3690
                *          *          *          *          *          *          *
B. amyloliq.  agaaa--------gtcaaac------gaaacaggaatgaacctttcccgcgcatacaaataggagaaaggttttttt
B. subtilis   ....-----------a.g.t.t-------a.g.t.t.....a..........c...tt.................
B. lichenif.  c....tagaatatcg......atgcaa.t.t...tc.........c......tcg......ga.............c 3700       3710
                *          *
B. amyloliq.  gattttgatagaaa-agactgcct
B. subtilis   -..a..a....ttg..ga..a--
B. lichenif.  atg.a..ccga...-.att.c...
```

EXPRESSION SYSTEM FOR THE ANTIBIOTIC-FREE PRODUCTION OF POLYPEPTIDES

The present invention relates to a microbial expression system for the production of polypeptides based on the use of extrachromosomal DNA, whereby no antibiotic marker genes (genes whose derived proteins provide the cell with resistance to an antibiotic, also named antibiotic-resistance genes, resistance genes, antibiotic maker or antibiotic selection marker) for the selection of the host cell but DNA sequences that code glycerine-3-phosphate dehydrogenase (also named NAD(P)H-dependent dihydroxyacetone phosphate reductase, NAD(P)H-dependent glycerine-3-phosphate dehydrogenase, glycerine-3-phosphate dehydrogenase (NADP), glycerine-3-phosphate synthase, biosynthetic glycerine-3-phosphate dehydrogenase, L-glycerine-3-phosphate: NAD(P) oxidoredutase) are used, and, thus, the production of the desired polypeptide, e.g., xylanase, does not need the addition of antibiotics. The expression system is free from antibiotic-resistance genes. The invention further relates to a DNA sequence that codes a polypeptide with glycerine-3-phosphate dehydrogenase activity as well as a polypeptide with glycerine-3-phosphate dehydrogenase activity.

Polypeptides and enzymes that are needed in large amounts are today mainly obtained by fermentation of micro-organisms. Two groups of micro-organisms are hereby used—i) such micro-organisms that the proteins of interest naturally produce, and ii) genetically modified micro-organisms. The genetic methods that are necessary for the modification of the micro-organisms have been known in the state of the art for a long time. The principle thereof is that genes that code for the proteins of interest are inserted into the host cells and transcribed, translated, possibly post-translationally modified and optionally secreted by the respective membranes into the periplasm or the adjacent medium by the host cells. The polypeptides of interest may then be isolated from the respective cells or the culture supernatants.

In technical methods for the production of polypeptides first the natural abilities of the micro-organisms used for the production are exploited for synthesis and optionally for secretion of the proteins. Such systems that are cost-effective in the fermentation, show a high product-formation rate and promise a correct folding, modification etc. of the polypeptide to be produced are basically selected as systems for the production of polypeptides. The established micro-organisms for this are either of eukaryotic origin such as, e.g., filamentous fungi (*Aspergilla, Trichoderma, Penicillium*) and yeasts (e.g. *Saccharomyces, Hansenula, Pichia*) or prokaryotes are used such as, e.g., *E. coli, bacilli, lactobacilli, staphylococci, streptomycetes* or *pseudomonades*.

The profitability of a biotechnological method decisively depends on the obtained yield of polypeptide. This yield is not only determined by the used expression system but also by the used manufacturing process, particularly by the fermentation parameters and the culture media. By optimizing the expression system and the fermentation process, the potential and the obtainable yield may be clearly increased.

Genetically modified micro-organisms contain the new genetic information either integrated into the genome as it is often the case for filamentous fungi or yeasts or on extrachromosomal elements such as, e.g., plasmids that are often used in prokaryotes or also yeasts. The first constructs, in which the new genetic information is integrated into the host genome, are also very stable without selection pressure. The disadvantage of this method for prokaryotes is that only one copy of the gene is present in the host after the transformation and the integration of further copies of the same gene for increasing the product-formation rate via the gene-dosage effect is methodically very complex. A solution to this approach may be found in EP 0 284 126 B1, which solves the problem of the stable multiple integration of a gene by separately providing the copies of the exogenous gene to be integrated into the host cell genome by endogenous chromosomal DNA that is vital for the cell. The patent application DD 277467 A1 provides a method for the production of extracellular enzymes, which is based on the stable, advantageously multiple integration of the genes that code for the polypeptide of interest into the bacterial chromosome. The integration is hereby carried out by recombination via homologous ranges. An erythromycine gene that is contained on the plasmid by which the genes are inserted into the cell and inactivated in case of a successful integration serves as a control of the successful events of integration.

The application WO 96/23073 A1 discloses a system based on transposition for the integration of several copies of a gene of interest into the bacterial chromosome characterized in that the marker genes of the vector are deleted during or after the integration and, thus, the obtained strains are free from a marker gene. According to this document, a maker is only needed during the construction of the respective bacterial strain.

A system for increasing the number of copies of certain genes integrated in a bacterial chromosome is disclosed in the application WO 01/90393 A1.

If extrachromosomal DNA is used for the production of a genetically modified micro-organism, the gene of interest is transferred to an autonomously replicating element, for example, a plasmid, and episomally maintained in the host organism. The gene-dosage effect via the usually high number of plasmid copies per cell advantageously influences the yield of the polypeptide that is coded by the gene of interest. Disadvantageous is the fact that a selection pressure is to be maintained over the complete culture time to maintain the extrachromosomal elements stable in the cell. As standard this takes place by adding antibiotics to the culture medium. Since the gene by which the micro-organism becomes resistant to the antibiotic is located on the extrachromosomal element, only the cells that have such an element may grow. The gene of interest is maintained in the cells in a high number of copies by locating it on the same plasmid by which the hosts become resistant to the antibiotic/antibiotics. By using antibiotics as selection pressure, losing the plasmid due to segregative or structural instability may be avoided (Bron and Luxen, 1985, plasmid 14, 235-244). In this way larger plasmids may also be maintained stable in the cell and the cell maintains the ability to produce the desired polypeptide. Generally, a loss of extrachromosomal DNA takes place very easily, particularly if it is about DNA that is unknown to this organism. As regards bacteria that naturally contain plasmids, the application of selection pressure is also often reasonable, since the naturally occurring, extrachromosomal elements are often only present in a low number of copies; however, a high number of copies is necessary for a commercially high production rate. This high number of copies can, however, usually only be maintained by a selection pressure.

The use of antibiotic resistances as selection marker has been considered more an more critically in recent years. Firstly, the use of antibiotics is rather expensive, particularly if the resistance is based on an enzyme that degrades the antibiotic, so that the antibiotic must be supplied during the whole cultivation. Secondly, their worldwide use, which also extends to other fields of engineering and medicine, contributes to the spreading of resistance genes on other, also pathogenic strains, which might have negative consequences on disease control.

Antibiotic-free selection system have also already been developed in the prior art. For example, the publication by Herrero et al. (1990, J. Bacteriol. 172, 6557-6567) describes resistances to herbicides and heavy metals as selection marker. However, the same concerns as against antibiotics argue against the use of these compounds.

Another applied method to maintain plasmids stable in the cell is the episomal complementation of auxotrophic strains. In this case genes of the genome of the production strain that code for essential metabolic functions are removed or inactivated. The thus auxotrophic host strains may only grow if the metabolite function is alternatively reproduced. The necessary metabolic product may, e.g., be added to the medium if the strain is able to accept this metabolite or the gene that is deactivated on the host genome and that codes the essential function may be made episomally available. Advantageously, this takes place on the plasmid that also carries the gene of interest for a polypeptide production. The patent EP 0 284 126 B1 lists the metabolic genes leu, his, trp or the like, particularly those from amino acid synthesis ways, as auxotrophic selection markers.

In practice the use of such auxotrophies as selection markers has been very difficult so far, since particularly in industrial fermentation media almost all necessary substances such as amino acids and vitamins are available in sufficient amounts and the respective cells may balance the inability of synthesis of a certain metabolite by absorption of this metabolite from the culture medium.

The industrially used fermentation media usually contain components that are waste products of other, often fermentative processes, e.g., grain residues from the ethanol production (distillers spent grain), corn residues from the starch production (corn steep powder or corn steep liquor) or potato residues from the starch production (potato slump). These components not only serve as carbon source (C) or nitrogen source (N) but are also often rich in, e.g., vitamins or amino acids due to the microbial fermentation that was involved in their recovery. The industrially used fermentation media are consequently very complex. It is, thus, difficult if not even impossible to maintain a selection pressure in these media even if auxotrophic strains are used.

So far the only exceptions are auxotrophies for the essential thymidine and D-alanine necessary for Bacilli and gram-positive micro-organisms, which are only present in traces or not at all in industrial fermentation media and, thus, must be produced by micro-organisms themselves. Therefore, the application EP 0 251 579 A1 provides the solution to use as host strains such strains that are deficient as regards the gene essential for the nucleotide metabolism for the thymidylate synthase. Accordingly, the gene may be made available for this function (thyA from *Escherichia coli* K12) by means of a vector and cure the gene defect. The patent EP 0 185 512 B1 solves the problem by the insertion of the dal gene (D,L-alanine racemase) into the plasmid using dal-deficient host strains.

A further solution to this problem was described in the application WO 2004/078953. It disclosed that the essential factors involved in the secretion were suitable for a selection. A gene whose derived protein is involved in the protein translocation as a factor that is essential for the respective gene, e.g., regarding *Bacillus*, the proteins SecA, SecY, SecE, b-SRP, FtsY or PrsA, provides a basis for the selection, This means that the failure of such a factor is lethal and, thus, allows for an antibiotic-similar selection of the recombinant micro-organisms.

All in all it must be stated that in spite of experience in the production of polypeptides by biotechnological methods for years, so far there has not been provided a practicable system in which a production with a high number of copies of the gene of interest without selection by expensive or ecologically questionable substances such as antibiotics is possible. So far the different approaches for the selection by auxotrophic markers have also resulted in meager results due to the complex culture media used in the industry (WO 2004/078953) or the systems still contain antibiotic-resistance genes.

The use of defined media composed of purified components (pure C-sources and N-sources as well as vitamins, amino acids and minerals) is not possible for the production of industrially used polypeptides such as, e.g., enzymes in the food industry, feed industry or detergent industry because of the high costs thereof.

Therefore, it is the object of the present invention to provide an expression system for the production of polypeptides in which there is no selection by expensive and/or polluting and/or unhealthy substances. A selection is not to take place by antibiotic resistances, in particular. The expression system according to the invention is to be easily applicable and universally suitable for the expression of any target polypeptides. Furthermore, the expression system according to the invention is to be suitable for the establishment in any host cells. Moreover, the expression system according to the invention is also to allow for a selection in industrially usual or cost-effective culture media.

The object is solved by an expression system for the production of one or more target polypeptide/target polypeptides, comprising a host cell in whose genome the DNA sequence that codes glycerine-3-phosphate dehydrogenase is inactivated or partially or completely deleted and which is transformed by an extrachromosomal element that comprises a DNA sequence that codes the target polypeptide(s) and glycerine-3-phosphate dehydrogenase, whereby not only the host cell genome but also the extrachromosomal element carry no antibiotic-resistance gene.

It was surprisingly found that a glycerine-3-phosphate dehydrogenase gene that is provided on an extrachromosomal element may be used in the respective auxotrophic host cells for the selection of the corresponding host cells. The extrachromosomal element that carries the glycerine-3-phosphate dehydrogenase gene also carries the gene for the polypeptide of interest to be produced.

Therefore, the glycerine-3-phosphate dehydrogenase gene serves as selection marker for stabilizing the extrachromosomal element in the auxotrophic host cells. This stabilization of the extrachromosomal element, which comprises a DNA sequence that codes the target polypeptide(s) and glycerine-3-phosphate dehydrogenase, is based on the episomal complementation of the host cell turned auxotrophic. In the genome of the host strain a DNA sequence that codes glycerine-3-phosphate dehydrogenase or a respective gene is inactivated. This gene codes the enzyme glycerine-3-phosphate dehydrogenase (also NAD(P)H-dependent dihydroxyacetone phosphate reductase; glycerine-3-phosphate synthase, biosynthetic glycerine-3-phosphate dehydrogenase; Morbidoni et al., 1995, J. Bacterial. 177 (2), 5899-5909; EC numbers 1.1.1.8, 1.1.1.94, here also, inter alia, NAD(P)H-dependent glycerine-3-phosphate dehydrogenase, glycerine-3-phosphate dehydrogenase (NADP), L-glycerine-3-phosphate: NAD(P) oxidoreductase). The glycerine-3-phosphate dehydrogenase catalyzes the conversion of dihydroxyacetone phosphate to sn-glycerine-3-phosphate under linkage of NAD(P)H. sn-glycerine-3-phosphate itself is the starting substance for the phospholipid synthesis of the cell and, thus, central metabolite for the cell membrane synthesis. Depending on the organism, the gene for the NAD(P)H-dependent glycerine-3-phosphate dehydrogenase is, inter alia, referred to as gpsA (also named gol, gly, glyc), gpd (gpd 1/2/3/A/A1/A2/h) or dart Generally, it is the enzyme that catalyzes the synthesis of glycerine-3-phosphate under physiological conditions and usually uses NAD(P)H as co-factor. A corresponding enzyme that uses a different co-factor, e.g., FAD, would be also conceivable. Depending on the host strain, the corresponding gene that codes glycerine-3-phosphate dehydrogenase or the glycerine-3-phosphate dehydrogenase genes is inactivated.

By deleting the glycerine-3-phosphate dehydrogenase gene in the genome of the host strain, this strain becomes auxotrophic for glycerine-3-phosphate (G3P), may, however, grow if the culture medium is correspondingly supplemented (with G3P or glycerine) or the corresponding gene is episomally provided. By inserting the glycerine-3-phosphate dehydrogenase gene into the plasmid, which also carries the DNA sequence for the polypeptide of interest, the plasmid is maintained stable in the auxotrophic host cell. Concurrently, the antibiotic-resistance genes, which usually exist on plasmids, are eliminated. Furthermore, antibiotic-resistance genes that are optionally present in the genome of a host cell are also eliminated. The elimination of the antibiotic-resistance genes is carried out in a way known per se, for example, from the genome by homologous recombination (see below) or from the plasmid by excision by means of suitable restriction enzymes and subsequent ligation.

The respective DNA sequence that codes glycerine-3-phosphate dehydrogenase is deleted in the genome of the host cell of the expression system according to the invention. The deletion may be complete or partial. In any case the deletion must be present to the effect that the glycerine-3-phosphate dehydrogenase gene is inactivated. The inactivation of this gene in the host strain takes place by homologous recombination with an inactivated or (partially) deleted gene copy, for example. As a result of this recombination event, the chromosomal copy of the gene becomes inoperable. Moreover, preferred systems are characterized in that the inactivation of the glycerine-3-phosphate dehydrogenase gene on the chromosome takes place to the effect that a later recombination between the inactivated chromosomal gene copy and the homologous regions on the curing complementation vector is avoided, preferably at a complete loss of the gene or gene section comprised in the respective chromosomal locus. A recombination and integration of the complementation vector into the genome of the host by which the cell is episomally provided with the essential function would cure the inactivation again and, thus, offset the selection pressure by which the plasmid is maintained stable in the cell. The gene actually of interest and to be expressed could thereby be lost by the subsequent cell divisions or be only present in one or few copy/copies on the chromosome. This is prevented by an extensive or complete deletion during the inactivation step, which may theoretically also involve DNA sections that are located upstream or downstream. It must thereby be taken into consideration that the regions upstream or downstream of the gpsA gene may have functions in the host strain that are also essential to the host.

To exclude a homologous recombination between the glycerine-3-phosphate dehydrogenase gene provided by the extrachromosomal element and an optionally present chromosomal gene, it is necessary to inactivate the glycerine-3-phosphate dehydrogenase gene on the host genome not only by individual point mutation but to remove it extensively or completely. The elimination of the gene from the host genome is, for example, carried out by homologous recombination by means of a deletion vector comprising only an inactive part of the gene or even better only the flanking regions of the gene without the gene itself, so that the gene copy on the host genome is replaced with the truncated copy present on the deletion vector or completely deleted. It is essential that no antibiotic marker genes are hereby left behind. To eliminate the gene completely from the host, it is necessary to isolate the regions that flank the gene upstream and downstream from the host genome and to insert these flanking regions without the glycerine-3-phosphate dehydrogenase gene itself into a deletion vector. Then the homologous recombination takes place between the sequences flanking the glycerine-3-phosphate dehydrogenase gene, whereby the glycerine-3-phosphate dehydrogenase gene is completely removed from the genome.

According to the invention, the glycerine-3-phosphate dehydrogenase gene deleted or inactivated on the host chromosome is again made available to the cell on an extrachromosomal element also carrying a DNA sequence that codes a polypeptide of interest. Not only the same gene that was deleted in the respective host cell but also a corresponding gene that codes for NAD(P)H-dependent glycerine-3-phosphate dehydrogenase may be made available to the host cell again.

Therefore, the invention also relates to a vector for the complementation of the genome of a host cell in which the DNA sequence that codes glycerine-3-phosphate dehydrogenase is deleted, comprising a DNA sequence that codes the target polypeptide(s), and an expression cassette that comprises a DNA sequence that codes glycerine-3-phosphate dehydrogenase, whereby the vector does not contain antibiotic-resistance genes. Thus, the vector cures the inactivation of the DNA that codes the glycerine-3-phosphate dehydrogenase ("complementation vector"), i.e., it provides extrachromosomally an active gene copy that codes glycerine-3-phosphate dehydrogenase. The terms "vector" and "plasmid" are basically used interchangeably. Other extrachromosomal elements such as, e.g., phages, pagmides or transposons may also serve as vectors.

A plasmid that maintains a high number of copies in the host cell is preferred as vector. It is particularly advantageous if the plasmid is a plasmid establishing in a manifold (for example, 10 to 30 plasmids per cell), preferably in a multiple number of copies (more than 30 plasmids per cell). The more plasmid copies are present, the higher is the yield of the desired protein product due to the gene-dosage effect.

According to the invention, the complementation vector is not to contain any antibiotic-resistance genes. Moreover, the complementation vector contains not only the sequences of interest for the polypeptide production but also an expression cassette with the glycerine-3-phosphate dehydrogenase gene.

Preferably, the deleted sequence that codes the glycerine-3-phosphate dehydrogenase and is endogenously present in the host cells is hereby used. It is however, also possible to use sequences of other organisms that code an enzyme having the same function, preferably of related strains, if they are able to cure the respective defect and thereby provide a system that guarantees a high productivity of the protein of interest without further selection pressure. A loss of this extrachromosomal DNA would be lethal for the auxotrophic host cell if grown in minimal medium, so that such a cell is forced to transmit this extrachromosomal element on to the following generation in each cell division. There is an endogenous selection pressure in the system according to the invention as long as the recombinant strain grows in a medium without provision of glycerine-3-phosphate or glycerine. It is not necessary to add an antibiotic to avoid the loss of the vector with the gene to be expressed.

The expression cassettes that may be used for the introduction of a DNA sequence that codes the activity of a glycerine-3-phosphate dehydrogenase or an open reading frame according to the invention into a host cell preferably comprise a transcription start region that is linked to the open reading frame. Such an expression cassette may comprise a variety of restriction cleavage sites for the insertion of the open reading frame and/or other DNA, e.g., a transcription regulation region. The transcription cassette comprises in 5'→3' direction of the transcription a transcription and translation start region, the DNA sequence that codes for the glycerine-3-phosphate dehydrogenase activity and a transcription and translation stop region that is functional in a microbial cell. The termination region may be native regarding the transcription initiation region, may be native regarding the DNA sequence of interest or may be derived from any other source.

The term "open reading frame" (ORF) refers to the amino acid sequence that is coded between the translation start and stop codons of an encoding sequence, The terms "start codon" and "stop codon" refer to a unity of three adjacent nucleotides (codons) in a coding sequence, which specify the chain start and stop of the protein synthesis (mRNA translation).

In connection with a nucleic acid "operable linkage" refers to a compound as part of the same nucleic acid molecule in suitable position and orientation to the transcription start of the promoter. DNA in operable linkage to a promoter is located below the transcription initiation regulation of the promoter. Coding sequences may be operably linked to the regulator sequence in sense or antisense orientation. With reference to polypeptides, operable linkage means the compound as part of the same polypeptide, i.e., via peptidyle bonds.

According to the invention, any promoters may be used as long as they maintain the system according to the invention stable. In the preferred embodiment weak and constitutive promoters are used. Promoter usually refers to the nucleotide sequence upstream (5') as regards the coding sequence and controls the expression of the coding sequence by providing the recognition of the RNA polymerase and other factors that are necessary for the correct transcription. The promoter used according to the invention may comprise a minimal promoter, i.e., a short DNA sequence from a TATA box and other sequences that specify the transcription start site to which regulator elements are attached to control the expression.

With the expression system according to the invention the polypeptide of interest may be produced with a higher, but at least the same yield without the addition of antibiotics at any point of the production and without antibiotic marker genes being present and without antibiotics or antibiotic-resistance genes being present in the protein product. By using the expression system according to the invention, the products may, therefore, also be used in applications in which the presence of complete or partial antibiotic marker genes is not admissible or not desired.

The invention further relates to the use of the expression system for the antibiotic-free production of the target polypeptide. The expression system is thereby grown in a medium that is free from glycerine-3-phosphate or glycerine-3-phosphate-providing compounds. Examples of such media are stated above. The growing of the expression system is carried out in a way known per se.

The expression system according to the invention is suitable for any host cells. The expression system according to the invention may generally be used for practically all industrial host cells that are important for fermentative protein production. Examples are Gram-positive host organisms, for example, of the genus *Staphylococcus, Corynebacterium* or *Bacillus*, particularly the species *Staphylococcus carnosus, Corynebacterium glutamicum, Bacillus subtilis, B. licheniformis, B. amyloliquefaciens, B. brevis, B. globigii, B. megaterium, B. clausii* or *B. lentus*, and very particularly derivatives of the strains *B. licheniformis* or *B. amyloliquefaciens*.

The use of *Bacillus* strains as host cells is preferred. Particularly preferred is the use of *Bacillus amyloliquefaciens*. In *Bacillus amyloliquefaciens* the glycerine-3-phosphate dehydrogenase gene is present as gpsA. It was surprisingly found that the expression system according to the invention may be established in *Bacillus amyloliquefaciens* without a reduction of the number of copies of the production plasmid compared to the analogous antibiotic-marker-containing plasmid (pUB110 derivative). It was rather possible to obtain a higher productivity with a thus trans-formed *B. amyloliquefaciens* host strain (GpsA$^-$), even if compared to the host strain transformed by the starting plasmid with antibiotic marker gene (pIK91 derived from pUB110, see EP 0 585 617 B1) (GpsA$^+$).

It was further found that the endogenous gpsA gene of *Bacillus amyloliquefaciens* may be best removed from the genome of *Bacillus amyloliquefaciens* by use of the sequences flanking this gene. Moreover, it is advantageous if the endogenous gpsA gene as such is provided episomally. The gpsA gene from *B. amyloliquefaciens*, which has been unknown so far, was isolated for this purpose. Although sequence databases such as, e.g., EMBL (European Bioinformatics Institute (EBI), Cambridge, Great Britain) or GenBank (National Center for Biotechnology Information NCBI, National Institutes of Health, Bethesda, Md., USA) contain gpsA gene data, a comparison of the gene according to the invention with gpsA genes from other organisms shows only 76% identity on DNA level with the gene described for *Bacillus subtilis* or 71% identity with the gene of *Bacillus licheniformis*.

The enzyme glycerine-3-phosphate dehydrogenase provides in Bacilli sn-gylcerine-3-phosphate (G3P), an essential metabolite of the cell membrane synthesis. Morbidoni et al. (1995) describe that the G3P content in the *Bacillus subtilis* cell must be regulated very finely and that the balance between synthesis and degradation of G3P in the cell is very critical. Experiments by Freese et al. (1972, in: Halverson et al, (ed.) Spores V, 212-221) show that *B. subtilis* cells in which glycerine phosphate accumulates due to a defect of the catabolic glycerine phosphate dehydrogenase (G of) grow worse than normal cells and that the sporulation is suppressed.

It is generally desirable that the gene of interest that codes the polypeptide to be produced is present in the host cell in a possibly high number of copies to increase the yield via the gene-dosage effect. Thus, in a preferred embodiment plasmids that are present in the cell with various copies are used such as, e.g., derivatives of pUB110, which is present with about 50 copies per cell (Gryczan et al., 1978, J. Bacterial. 134, 318-329). The introduction of such numerous copies of the gene gpsA to be complemented could, however, disturb the sensitive balance between synthesis and degradation of G3P.

It has now surprisingly been found that these problems described for *Bacillus subtilis* do not occur in *Bacillus amyloliquefaciens* under the conditions according to the invention. In a preferred embodiment the gpsA gene is thereby placed below a weak promoter. Zyprian and Matzura (1986, DNA 5, 219-225) report that in the vector pUB110 such a promoter is naturally present. If the gpsA gene is put under the regulation of this promoter, the delicate balance between synthesis and degradation of G3P in the cell is apparently maintained despite an increased number of gene copies compared to a non-modified *Bacillus* cell. Since the promoter is also constitutive, sufficient glycerine-3-phosphate dehydrogenase is provided in the cell cycle of *Bacillus* at any point in time. Moreover, this system also results in a stable maintenance of the high number of copies in the gpsA-negative host cell if grown in complex medium. This allows for the production of polypeptides of interest, which are also coded by the complementing vector, in high concentrations in the culture media usually used by the industry.

As already stated, according to the invention any promoters may be used as long as they maintain the system according to the invention stable. Weak, constitutive promoters are particularly preferred such as, e.g., the aforementioned promoter described for the plasmid pUB110 by Zyprian and Matzura (1986). The ptsH promoter from *B. subtilis* is also a suitable weak and constitutive promoter (Stülke and Hilien, 2000, Annu. Rev. Microbiol. 54, 849-80).

As set forth above, in the expression system according to the invention the glycerine-3-phosphate dehydrogenase gene is inactivated on the host chromosome. The inability to synthesize of glycerine-3-phosphate dehydrogenase is equated by an episomal provision of the respective gene. GpsA-negative *Bacillus subtilis* mutants were already produced by classic mutation a long time ago (Mindich, 1970, J. Mol. Biol. 49, 415-432). These mutations are alleles of the gpsA gene (Morbidoni et al., 1995), which have probably only point mutations in the gpsA gene or its regulation.

These strains (and this method) are not useable for an industrial protein production, since there might be spontaneous back-mutation to the active form as well as recombination of the intact, episomally provided gpsA gene with the defective chromosomal gene due to the long homology regions (cf. also Ostroff et al., 1984, Mol. Gen. Genet. 193, 299-305). Khasanov et al. (1992, Mol. Gen, Genet. 234, 494-497) showed that there might already be a homologous recombination in the genome at homologies of 70 bp in *Bacillus*. In such a case the host cells could become prototrophic again and would not longer be dependent on the plasmid with the gpsA gene. This could lead to an easier integration or the loss of the plasmid, so that the polypeptide of interest, the gene of which is also present on the plasmid, may be no longer produced by the host cell or only in small amounts.

The gpsA gene as well as the regions upstream and downstream of the gene are not described for *Bacillus amyloliquefaciens*; the databases (e.g., EMBL, GenBank, SubtiList (Moszer et al., 1995, Microbiology 141, 261-268, Moszer, 1998, FEBS Lett. 430, 28-36) only provide data on *Bacillus subtilis* and micro-organisms that are more distantly related. The organisation of the genome of *B. amyloliquefaciens* is not known either. Genes that are located on the chromosome of *B. subtilis* in direct vicinity to the gpsA gene, i.e., that represent the flanking regions necessary for the production of the auxotrophic host may be present in the genome of *B. amyloliquefaciens* at completely different positions or may even be missing at all. It is also to be taken into consideration that the regions upstream and downstream of the gpsA gene may code functions in the host strain that are essential for the host. For *B. subtilis* genes with unknown functions are described upstream and downstream, while there is no information on adjacent genes for *B. amyloliquefaciens*. It is, thus, advisable to completely maintain the regions adjacent to the gpsA gene for *B. subtilis* and also for *B. amyloliquefaciens* and other Bacilli to destroy no other unknown and thus not complementable functions of the genome. A complete but possibly precise deletion of the gpsA gene that does not cause any mutation or reading frame shift in the possibly adjacent genes is, thus, to be aspired according to the invention.

A homogenous recombination for the precise removal of a chromosomal gene or gene fragments will be the more successful the longer the homologous regions are (cf. Hamilton et al., 1989, J. Bacterial. 171 (9) 4617-4622). It was found that the regions flanking the gpsA gene from *B. amyloliquefaciens* only show a sequence identity of about 84% for the region of about 1.3 kbp upstream and an identity of about 69% for the region of about 1.1 kbp downstream with the corresponding regions from *B. subtilis*—as described in the databank SubtiList (Moszer et al. 1995; 1998). The amplification of the flanking regions on the chromosomal DNA of the host strain *B. amyloliquefaciens* was, thus, extremely difficult, particularly since possibly long homologous regions for the construction of the deletion vector were to be produced.

The deletion of the glycerine-3-phosphate dehydrogenase gene on the host chromosome was carried out, for example, by means of plasmid vectors having a replication origin that is a temperature-sensitive or does not work in Bacilli and in which the possible (flanking) homologous DNA regions of the gene to be deleted were additionally inserted (deletion vector). A reversible inactivation, for example, by integration of a mobile genetic element, for example, a transposon, into the gene to be inactivated would, however, also be conceivable.

Methods for the inactivation of genes via a deletion vector are described in the publication by Vehmaanperä et al. (1991, J. Biotechnol. 19, 221-240). The replication origin of this deletion vector is characterized by its temperature dependency. It is, thus, possible the select for a successful transformation at low temperature first and then to exercise a selection pressure for a successful integration by increasing the temperature. Then the cell is cured by the vector comprising the endogenous gene copy, so that no functioning gene copy is any longer present on the chromosome. There do not remain any vector sequences, i.e., also no antibiotic-resistance genes, in the cell either.

Therefore, the invention relates to a DNA sequence that codes for a polypeptide with glycerine-3-phosphate dehydrogenase activity characterized in that the DNA sequence is selected from a) DNA sequences comprising a nucleotide sequence according to SEQ ID NO: 1, b) DNA sequences comprising a nucleotide sequence represented by the nucleotides 1338 to 2375 of SEQ ID NO: 1, c) DNA sequences coded by the plasmid pTP01 with the plasmid map according to FIG. 4 and deposited under the deposition number DSM 18890, d) DNA sequences coding for the protein sequence according to SEQ ID NO: 2, e) DNA sequences hybridizing under stringent conditions with one of the DNA sequences according to a), b), c) or d), f) DNA sequences related to the DNA/nucleotide sequences according to a), b), c), d) or e) due to the degeneracy of the genetic code, and g) complementary strands to the sequences according to a) to f), as well as a polypeptide with glycerine-3-phosphate dehydrogenase activity selected from a) a polypeptide that is coded by the coding part of the above DNA sequence, b) a polypeptide with the sequence according to SEQ ID NO: 2 or a sequence derived therefrom, which may be obtained by substitution, addition and/or deletion of one or more amino acids, c) a polypeptide with a sequence having at least 77% identity to the amino acids 1 to 345 of SEQ ID NO: 2, d) a polypeptide that is coded by a nucleic acid sequence that hybridizes under stringent conditions with (i) the nucleotides 1338 to 2375 of SEQ ID NO: 1, (ii) a partial sequence of (i) having at least 100 nucleotides, or (iii) a complementary strand of (i) or (ii), e) a variant of the polypeptide with SEQ ID NO: 2 comprising a substitution, deletion and/or insertion of one or more amino acids, f) allelic variants to the amino acid sequences a) to e).

The invention further relates to the use of the above DNA sequence for the production of the expression system according to the invention. It was surprisingly found that a DNA sequence derived from *Bacillus amlyoliquefaciens* that codes for a polypeptide with glycerine-3-phosphate dehydrogenase activity is particularly advantageous in the production of the expression system according to the invention.

As regards the claimed sequences, the degree of the sequence identity is preferably analyzed by determining the number of residues of the shorter sequence involved in the comparison and having a "corresponding" counterpart in the other sequence. For the purposes of the present invention the identity is preferably determined in a way known per se using the usual algorithms. According to the invention, only the nucleotides that code the mature proteins or the amino acids of the respective mature proteins are used for a comparison. According to the invention, similar, preferably identical sequence counterparts were detected as homologous sequences by means of known computer programs. An example of such a program is the program Clone Manager Suite, which comprises the program part Align Plus and is distributed by Scientific & Educational Software, Durham, N.C., USA. A comparison of two or more DNA or amino acid sequences as defined above is thereby carried out under the option local alignment either according to the method FastScan-MaxScore or according to the method Neeldeman-Wunsch, keeping the default values. To calculate the identity, the program version "Clone Manager 7 Algin Plus 5" with the functions "Compare Two Sequences/Local/Fast Scan-Max Score/Compare sequences as DNA bases" or for amino acids "Compare Two Sequences/Local/Fast Scan-Max Score/Compare sequences as Amino Acids" is especially used according to the invention. Algorithms available from the following sources were thereby used: Hirschberg (1975, Commun. Assoc. Comput. Mach. 18, 341-343); Myers and Miller (1988, CABIOS 4, 11-17); Chao et al. (1992, CABIOS 8, 481-487).

The invention further relates to addition and/or deletion molecules of the above polypeptides with glycerine-3-phosphate dehydrogenase activity. Thus, a polypeptide modified according to the invention with glycerine-3-phosphate dehydrogenase activity may be obtained by adding further sequences at the N-terminal and/or C-terminal end or in the molecule, whereby the thus obtained polypeptides still show glycerine-3-phosphate dehydrogenase activity or must be able to complement the glycerine-3-phosphate-dehydrogenase-deficient strains. Hybrid molecules having further advantageous properties may thereby be produced.

According to the invention, sequences parts of the polypeptide with glycerine-3-phosphate dehydrogenase activity may also be deleted keeping the glycerine-3-phosphate dehydrogenase activity. The mutation, elongation and shortening may be carried out in a way known per se according to methods known per se in the art.

The production of such variants is generally known in the art. For example, amino acid sequence variants of the polypeptides may be produced by mutation in the DNA. Methods for the mutagenesis and nucleotide sequence modification are well known in the state of the art (cf., for example, Kunkel, 1985, Proc. Natl. Acad. Sci. USA 82, 488-492, Kunkel et al., 1987, Methods Enzymol, 154, 367-382, U.S. Pat. No. 4,873,192, Walker and Gaastra (ed.), 1983, Techniques in Molecular Biology, Mac Millan Publishing Company, New York). References on suitable amino acid substitution that do no affect the biological activity of the protein of interest may be found in the model of Dayhoff et al. (1978, Atlas of Protein Sequence and Structure. Net. Biomed. Res. Found., Washington D.C.). Conservative substitutions such as the replacement of one amino acid with another one having similar properties are preferred. These replacements may be divided in 2 main groups with 4 subgroups altogether, and a replacement in each subgroup is referred to as conservative replacement, which preferably does not affect the activity or folding of the protein.

| aliphatic | non-polar | G A P |
|           |           | I L V |
|           | polar and uncharged | C S T M N Q |
|           | polar and charged | D E |
|           |           | K R |
| aromatic  |           | H F W Y |

The terms "protein", "peptide" and "polypeptide" are essentially used interchangeably. A polypeptide or enzyme having glycerine-3-phosphate dehydrogenase activity is to refer to an enzyme that catalyzes the NAD(P)H-coupled reduction of dihydroxyacetone phosphate to glycerine-3-phosphate. The glycerine-3-phosphate dehydrogenase activity may be determined using any test method known per se in which one of these substrates or products is used (Morbidoni et al., 1995; Bergmeyer, 1970, Methoden der enzymatischen Analyse. Verlag Chemie, 426-227).

The invention further relates to DNA sequences that code a polypeptide with glycerine-3-phosphate dehydrogenase activity, comprising mutations, modifications or variations of the sequence according to SEQ ID NO: 1. Moreover, the invention also relates to sequences that hybridize under relaxed or stringent conditions with the above sequences. Stringent conditions are: hybridization at 65° C., 18 h in dextrane sulfate solution (GenescreenPlus, DuPont), then washing the filters for 30 min each, first with 6×SSC, twice 2×SSC, twice 2×SSC, 0.1% SDS and then with 0.2×SSC at 65° C. (membrane transfer and detection methods, Amersham).

Furthermore, the invention also relates to DNA sequences that are related to the above sequences according to the invention due to the degeneracy of the genetic code as well as allelic variants thereof. The degeneracy of the genetic code may result from natural degeneracy or from an especially selected codon usage. Naturally occurring allelic variants may be identified using well-known techniques of molecular biology such as, for example, the polymerase chain reaction (PCR), sequencing techniques and hybridization techniques.

A DNA sequence that codes a polypeptide according to the invention may be used to be deleted in any host cells and is subsequently made available again on the plasmid that also carries the gene of interest. After the deletion/inactivation of the glycerine-3-phosphate dehydrogenase gene, the host cells are characterized by the lack of the essential function of the glycerine-3-phosphate dehydrogenase.

The kind of construction of auxotrophic host strains according to the invention as described herein makes it possible to use a once produced auxotrophic microorganism strain, the chromosomal glycerine-3-phosphate dehydrogenase gene of which was inactivated, for continuously new transformations with similarly constructed, complementing vectors, which each time provide the same function curing the gene defect but carry each different genes for other polypeptides of interest to be produced. Thus, a very practical and versatilely usable production system is provided.

It is the meaning of the system to maintain a genetic element that is needed for the production of a polypeptide of interest without antibiotic selection pressure stable over more or many generations and maintain it in a high number of copies in the cell. This element is the plasmid that carries not only the glycerine-3-phosphate dehydrogenase gene but also the gene for the polypeptide to be produced.

The maintenance of this selection pressure is of advantage for the storage of the recombinant production strains. The inherent stability of the system is, however, sufficient to maintain the high number of copies in the production process and, thus, to guarantee high productivity.

In consequence of the high inherent stability, the system remains stable even without the application of selection pressure, i.e., even if grown in industrial medium (which may contain traces of glycerine) in the main culture, the yield of target polypeptide does not decrease during the time of cultivation, i.e., the complementation vector is maintained stable in the cell.

Of particular interest are expression systems according to the invention that are directed to certain products produced by the cultivation of the micro-organisms, particularly, polypeptides or proteins such as, e.g., hydrolytic enzymes or oxidoreductases, particularly preferred alpha-amylases, beta-amylases, maltogenic amylases, CGTases, xylanases, alpha-galactosidases, beta-galactosidases, phospholipases, phosphatases, phytases, endoglucanases, particularly endo-beta-1,4-glucanases, endo-beta-1,3(4)-glucanases, endo-1,2-beta-glucanases and endo-1,3-alpha-glucanases, cellulases, xylosidases, galactanases, particularly arabinogalactan-endo-1,4-beta-galactosidases and arabinogalactan-endo-1,3-beta-galactosidases, pectin-degrading enzymes, particularly pectinases, pectin esterases, pectinlyases, polygalacturonases, arabinanases, rhamnogalacturonases, rhamnogalacturonanacetylesterases, rhamnogalacturonan-alpha-rhamnosidases, pectate lyases and alpha-galacturonidases, mannanases, beta-mannosidases, mannan acetyl esterases, xylan acetyl esterases, other xylanases, arabinoxylanases, proteolytic enzymes such as proteases and peptidases, lipolytic enzymes such as lipases, digalactosid-diglycerol-esterases and cutinases, and other enzymes such as laccases and transglutaminases.

Therefore, the use of a system according to the invention in industrial methods, mainly for protein production, is of particular importance. Methods for the production of a protein by cultivation of cells of a micro-organism strain are generally known in the state of the art if the plasmid is based on a selection pressure as it can be established by antibiotics.

The invention further relates to a method for the production of a polypeptide of interest using the expression system according to the invention.

Protein production methods characterized in that the protein of interest is secreted into the adjacent medium are of particular importance. The processing of the obtained product is hereby significantly alleviated. It is, however, also a possible alternative according to the invention to solubilize the respective cells producing the protein subsequent to the actual production and to thus obtain the product.

It is a particularly advantageous aspect that a number of related micro-organisms is obtained by always carrying out the same kind of inactivation and curing but providing on the curing vector another gene that codes for another polypeptide of interest each time. In this way a once successfully developed system may be transferred to innumerable further manufacturing processes.

FIGURES

The enclosed figures explain the invention in more detail. It is shown in

FIG. 1: DNA sequence of the gpsA gene with flanking regions from *Bacillus amyloliquefaciens*; SEQ ID NO, 1
(italicized: gpsA gene, italicized/bold: putative RBS, bold: putative terminator)

FIG. 2: amino acid sequence coded by the gpsA gene according to FIG. 1, SEQ ID NO. 2

FIG. 3: alignment of the DNA sequence according to FIG. 1 with other known *Bacillus* gpsA regions
(*B. amyloliq.*: *Bacillus amyloliquefaciens* RH 1330 (SEQ ID NO: 1); *B. subtilis*: *Bacillus subtilis* 168 (SEQ ID NO: 17); *B. lichenif.*: *Bacillus licheniformis* ATCC 14580 (SEQ ID NO: 18))

FIG. 4: plasmid map of pTP01 with the deposited gpsA gene

Figure 5:
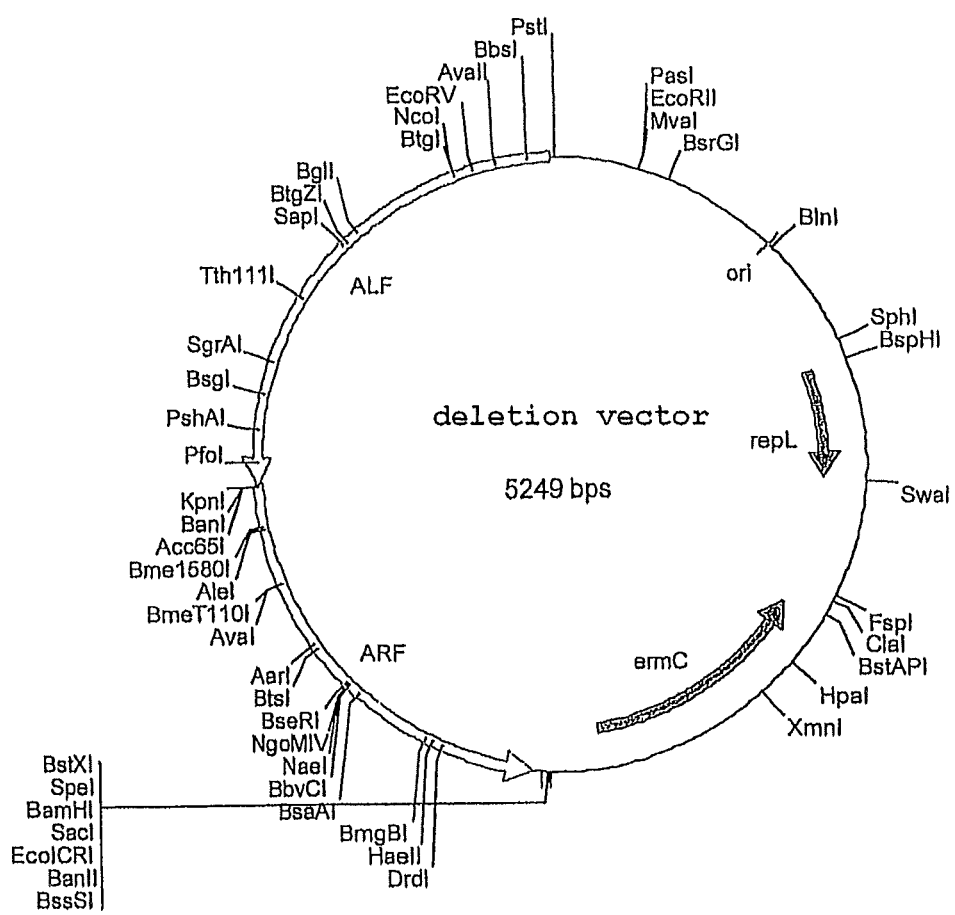

FIG. 5: plasmid map of the deletion plasmid
(ALF; region located upstream of the gpsA gene on the chromosome of *B. amyloliquefaciens* RH 1330; ARF: region located downstream of the gpsA gene on the chromosome of *B. amyloliquefaciens* RH 1330; ermC: the ermC gene codes an adenine-methylase providing resistance against erythromycine).

Figure 6:
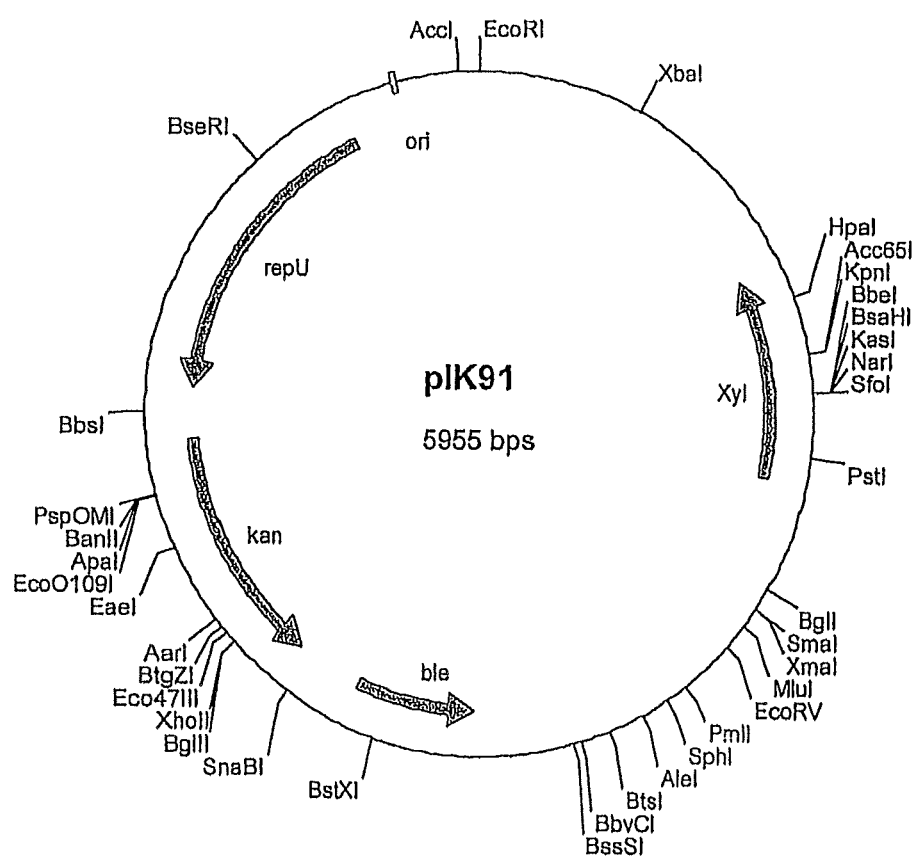

FIG. 6: plasmid map of pIK91

Figure 7:
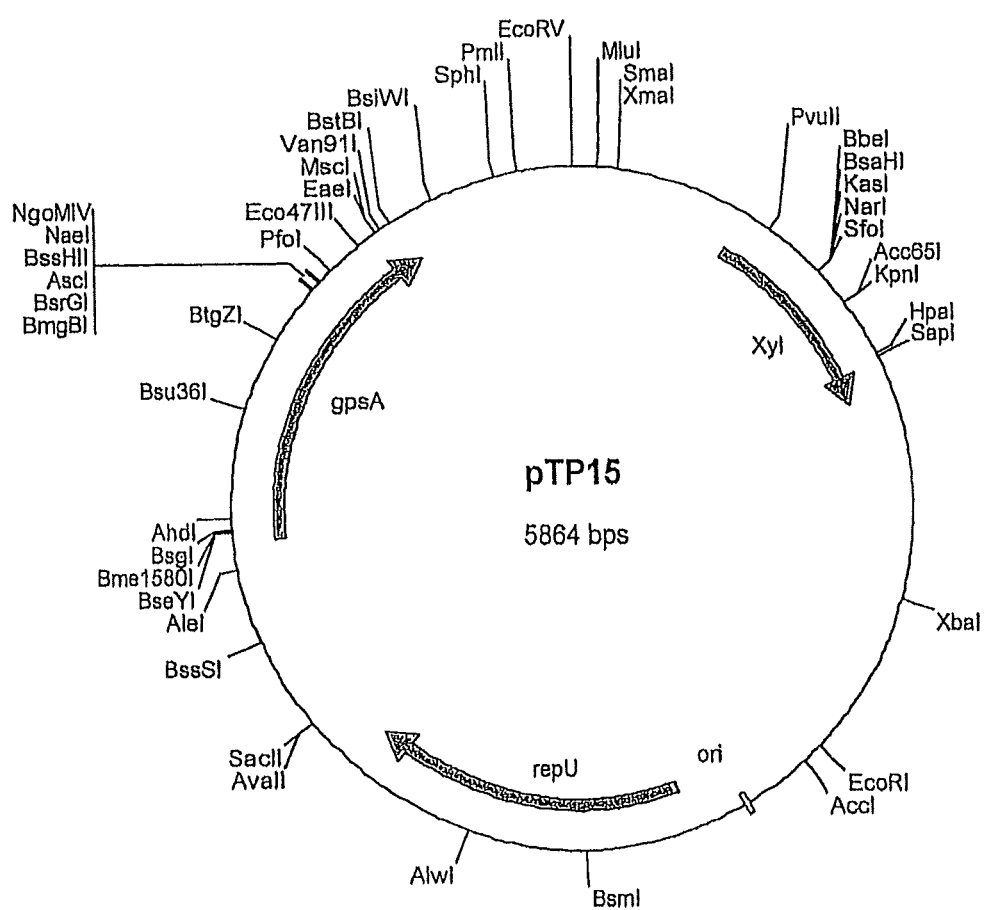

FIG. 7: plasmid map of the vector pTP15 used for the expression of the polypeptide The plasmid pTP01 of FIG. 4 and the strain RH 1626 were deposited at the DSMZ (Deutsche Sammlung von Mikroorganismen and Zellkulturen GmbH, Mascheroder Weg 1B, 38124 Braunschweig, Germany) on 22 Dec. 2006 or on 18 Dec. 2006 under the numbers DSM 18890 and DSM 18878. *Bacillus amyloliquefaciens* RH 1626, which was deposited under the number DSM 18878, is a recipient strain with a gpsA deletion and without plasmid. The deposition DSM 18890 relates to *Bacillus subtilis* RH 1632, which carries the plasmid pTP01.

The below examples explain the invention in more detail.

EXAMPLES

The molecular-biological works were carried out according to standard methods such as, for example, described in the manual by Sambrook and Russell (2001, Molecular cloning. Cold Spring Harbour Laboratory Press). The used kits and enzymes were applied according to the specification of the respective manufacturer.

Example 1

Isolation of the gpsA Gene from *Bacillus amyloliquefaciens*

To isolate the gpsA gene, chromosomal DNA from *Bacillus amyloliquefaciens* (AB Enzymes GmbH strain collection) was prepared by means of QIAGEN DNeasy Tissue Kit (Qiagen, Hilden), and the gpsA gene was hereon amplified via PCR. Primers that hybridize upstream and downstream of the gpsA gene were hereby used, so that the gene was completely amplified. The primers were derived from the sequences of the flanking regions of gpsA determined by sequencing in Example 2a). The following primers were used for the amplification:

```
SEQ ID NO. 3: AL_1198    gctgttaagccgccgagcttcgttg

SEQ ID NO. 4: AR_180C    taatcccatagcaccaagcgcaaaccac
```

The DNA fragment containing 1591 by was completely sequenced by the method according to Sanger et al. (1977, Proc. Natl. Acad. Sci. USA 74, 5463-5467). The used sequencing primers are listed in Table 1.

TABLE 1

Primers used for the complete sequencing of the gpsA gene from *Bacillus amyloliquefaciens*

| SEQ ID NO. | primer | sequence |
|---|---|---|
| 3 | AL_1198 | gctgttaagccgccgagcttcgttg |
| 4 | AR_180C | taatcccatagcaccaagcgcaaaccac |
| 5 | TPA fw 1 | cgacaaaagccattcgggaagtg |
| 6 | TPA fw 2 | tccgcgtctatacaaatcccg |
| 7 | TPA fw 3 | cgtaggcgatttaatcgtgac |

The gpsA gene being 1035 by long and the glycerine-3-phosphate dehydrogenase thus consisting of 345 amino acids is depicted with the flanking DNA regions in FIG. 1.

Example 2

Deletion of the gpsA Gene in *Bacillus amyloliquefaciens*

The elimination of the gene gpsA on the chromosome of *B. amyloliquefaciens* was carried out by a deletion vector. The procedure is based on the description of Vehmaanperä et al. (1991). The plasmid PE194, which was described in the same publication, was selected as vector for the gpsA deletion. It is the advantage of this vector that it has no temperature-dependent replication origin. At 28° C. pE194 may replicate in the cell, so that at this temperature it may first be selected for a successful transformation. Subsequently, the cells that contain the vector are incubated at 46° C. At this temperature the vector does no longer replicate, and a selection pressure is exercised on the integration of the plasmid over one of the two homologous regions (upstream and downstream of pgsA) into the chromosome. A further homologous recombination over the other (second) homologous region then leads to the gpsA deletion. A further recombination of the first homologous region would also be possible. Here the vector recombinates out of the chromosome again, so that the chromosomal gpsA gene would be maintained.

The elimination of the pgsA gene from the genome of *Bacillus amyloliquefaciens* RH 1330 comprises the following steps:

Step 1: Construction of the Deletion Vector
Isolation of the Regions Flanking gpsA from *Bacillus amyloliquefaciens*
The chromosomal DNA from *B. amyloliquefaciens* RH 1330 was prepared according to a specification by Sachse (in: Bertram and Gassen, 1991, Gentechnische Methoden. Gustav Fischer Verlag, Stuttgart, Jena, N.Y., 99-100).

The pgsA-flanking regions of *B. amyloliquefacines* RH 1330 were amplified on chromosomal DNA by PCR. Since the sequences of these regions of *B. amyloliquefaciens* were not available, different primers were derived from the known sequence of the yphC-gpsA-yphE-yphF region from *B. subtilis* (databank SubtiList (Moszer et al. 1995; 1998), state: Feb. 18, 2002). The primers were placed in non-coding regions (in *B. subtilis*) to avoid the introduction of mutations in genes within the flanking regions of the gpsA gene. Due to the particularly low sequence identity between *B. amyloliquefaciens* and *B. subtilis* in these non-coding regions, the amplification of the regions flanking the gpsA gene by PCR proved to be difficult and had, thus, to be carried out under very mild conditions (low annealing temperature, high template concentration).

The following primers were used for the PCR amplification of the region located upstream of the gpsA gene:

```
SEQ ID NO. 8
ALF.Xba.fw      aatgaaagcgtctagattgaaagg

SEQ ID NO. 9:
ALF.Kpn.bw      catgtttgattggtacctttttattttc
```

The PCR product (ALF, 1.4 kbp) was inserted into the plasmid pCR®2.1-TOPO® (Invitrogen, Carlsbad, USA). The resulting plasmid was named pCC1.

The following primers were used for the PCR amplification of the regions located downstream of the pgsA gene:

```
SEQ ID NO. 10:
ARF.Kpn.fw      aagcgaaggtacccctctttg

SEQ ID NO. 11:
ARF.Xba.bw      cctatttgaatatgacatctctagaaaatttc
```

The PCR product (ARF, 1.2 kbp) was inserted into the plasmid pCR02.1-TOPO®. The resulting product was named pCC2.

Incorporation of the Regions Flanking pgsA from *Bacillus amyloliquefaciens* in the Vector pE194

The ALF region was isolated from the plasmid pCC1 cut with Kpn I and inserted into the plasmid pCC2 cut with the same restriction enzyme. The regions flanking gpsA are present "head-to-tail" in the resulting plasmid pCC3.

The regions flanking gpsA were isolated from the plasmid pCC3 by restriction with Pst I and Sac I and built into the vector pE194 cut with the same restriction enzymes. The resulting temperature-dependent replicating plasmid pCC10 is a deletion vector. It was confirmed by restriction analysis and sequencing.

Step 2: Transformation of *B. amyloliquefaciens* with the Deletion Vector and Deletion of the gpsA Gene in the Chromosome

*C. amyloliquefaciens* RH 1330 was transformed by the deletion vector via protoplasts according to the method described by Chang and Cohen (1979, Mol. Gen. Genet. 168, 111-115).

Accordingly, the deletion of the gpsA gene was carried out according to the method described by Vehmaanperä et al. (1991). The deletion vector was first integrated into the chromosome under antibiotic pressure and temperature pressure by homologous recombination of one of the flanking regions of the gpsA gene. Subsequently, the cells without selection pressure were grown by erythromycine, which enabled a second recombination between the two copies of the second homologous region and lead to the excision of the deletion vector carrying the gpsA. The chromosomally coded gpsA gene was completely removed from the *Bacillus* genome in this way.

Finally, the cells in which the desired recombination events took place were isolated by examining the cells on their sensitivity to erythromycine and their auxotrophy for glycerine by growing on respective agar plates.

The isolated strain *B. amyloliquefaciens* RH 1330 Δ (gpsA) was named RH 1626. The absence of the gpsA gene and the conservation of the flanking regions in the chromosome of this strain as well as the absence of antibiotic-resistance genes and other sequences of pE194 were confirmed by sequencing and southern blot.

Example 3

Construction of the Recombinant Expression System

The construction of the recombinant expression system comprised the following steps:

Step 1: Insertion of the gpsA Gene into the pUB110 Derivative by *B. amyloliquefaciens* Xylanase The gpsA gene was amplified by its own ribosomal binding site (RBS) and its own transcription terminator starting from chromosomal DNA of *B. amyloliquefaciens*. The following primers were used for this purpose:

```
SEQ ID NO. 12:
ABa Ale fw          cgaatccggcacgcttgtggatttg

SEQ ID NO. 13:
ABa Sph bw          ccgtcccatcattgcatgcgttatatttc
```

The primers were constructed to the effect that upstream of the RBS an Ale I cleavage site and downstream of the terminator a Sph I cleaving site was inserted into the PCR product. Subsequently, the obtained PCR fragment could be cloned by these inserted cleavage sites into the xylanase expression vector pIK91 (EP0585617) behind the promoter described by Zyprian and Matzura (1986) for pUB110. The vector pIK91, a pUB110 derivative (McKenzie et al., 1986, plasmid 15, 93-103; McKenzie et al., 1987, plasmid 17, 83-85), comprises the gene for the endo-β-1,4-xalanase (xyl) of *Bacillus subtilis*, re-classified as *Bacillus amyloliquefaciens*. The plasmid pTP01 (depicted in FIG. 4) resulting from the cloning has a size of 7267 by and does not only carry the genes gpsA and xyl but also a kanamcycine-resistance gene and a bleomycine-resistance gene. The sequence of the resulting plasmid pTP01 was confirmed by restriction analysis and sequencing. A *Bacillus subtilis* strain (1A 247, BGSC; genotype: sacU (H), rpsL) was trans-formed by pTP01, whereby competent cells (Bertram and Gassen, 1991, Gentechnische Methoden. Gustav Fischer Verlag, Stuttgart, Jena, N.Y.) were used for transformation. The resulting strain was named RH 1632.

The expression of active glycerine-3-phosphate dehydrogenase in the pTP01-carrying *Bacillus* strain RH 1632 could be verified (contrary to previous reports in literature) by the enzyme activity test described by Morbidoni et al. (1995) and Bergmeyer (1970). In this activity test the change of the NADH concentration during the NADH-coupled conversion of dihydroxyacetone phosphate to sn-glycerine-3-phosphate catalyzed by glycerine-3-phosphate dehydrogenase is photometrically monitored. The decrease in the extinction at 340 nm is proportional to the decrease in concentration of the substrate. The *Bacillus* strain RH 1632 was hereby grown in a shaking flask on LB broth medium (1% peptone, 0.5% yeast extract, 1% NaCl, tap water, adjusting the pH value to pH 7.2 before the sterilization), the cells were collected by centrifugation, and solubilised by lysozyme. The cell lysate was used for the glycerine-3-phosphate dehydrogenase activity test. Using an analogous glycerine-3-phosphate dehydrogenase from rabbit muscle as standard, it could be shown that the plasmid-carrying *Bacillus* strain RH 1632 has an activity that is by 2.0 units $g^{-1}$ cells moist mass higher compared to *B. subtilis* 1A 247. Thus, the episomally coded gpsA gene is also expressed in the transformant additional to the chromosomally coded gpsA gene.

To review the complementing of the auxotrophic GpsA⁻ *Bacillus amyloliquefaciens* strain RH 1626 (Example 2) via pTP01, the strain RH 1626 was transformed with the plasmid pTP01 via protoplasts (corresponding to Chang and Cohen, 1979). The selection of the transformants was carried out by antibiotic selection on TYE agar plates, supplemented with xylane and kanamycin (1% peptone, 0.5% yeast extract, 0.8% NaCl, 1% xylane, 10 g/l kanamycin). The complementing of the to auxotrophic *B. amyloliquefaciens* strain via pTP01 was verified by the cultivation on minimum medium (Spizizen salt (Anagnostopoulos and Spizizen, 1961, J. Bacteriol. 81/5), 741-746) with 0.7% glucose and 0.4% glutamine, water purified by the Millipore Water System, pH value at pH 7.2 before the sterilization) without addition of glycerine or G3P.

Step 2: Deletion of the Antibiotic Marker Genes

The antibiotic-resistance genes kan and ble were removed from the plasmid pTP01 (Example 3, step 1) by amplifying the complete plasmid without genes kan and ble by PCR. Primers that inserted a Sac II cleavage site into the PCR product at each end of the PCR product were used for this purpose:

```
SEQ ID NO. 14:
pT ble kan Sac fw  gctaaaatctattattccgcggttcag-
                   caatcgg SEQ ID NO. 15:
pT kan ble Sac bw  gtccattcactatccgcggtcccttttcag
```

The obtained PCR product was cut with Sac II, and the restriction product was relegated. Protoplasts of the *B. subtilis* strain BGSC 61106 (gol (=gpsA) metC trpC2. Morbidoni et al., 1995) were transformed by the ligation, product. The strain BGSC 61106 acted as an intermediate host. A direct transformation of the ligation product in the auxotrophic GpsA⁻ *B. amyloliquefaciens* transformant strain RH 1626 (Example 2) was not possible. The selection of the *Bacillus* transformants was carried out on agar plates consisting of Spizizen salt, 0.7% glucose and 0.2% glutamine. The 5864 resulting by plasmid was confirmed by mapping and sequencing and was named pTP15 (FIG. 7).

Step 3: Preparation of a Recombinant Expression System

The isolation of the plasmid pTP15 from *B. subtilis* BGSC 61106 was carried out by QIAGEN Plasmid MinniprepKit. The *B. amyloliquefaciens* strain RH 1626 (ΔgpsA; Example 2) was transformed via protoplasts by the plasmid pTP15. The resulting host/vector system, which gets by without the presence of antibiotic-resistance genes and without antibiotics in the culture medium, was registered under the number RH 1810 in the AB Enzymes strain collection. The complementation of the auxotrophic *B. amyloliquefaciens* strain by pTP15 was verified by cultivation on minimum medium (Spizizen salt with 0.7% glucose and 0.4% glutamine, water purified by the Millipore Water System, pH value at pH 7.2 before the sterilization). RH 1810 grows on minimum medium as opposed to RH 1626. The absence of the gpsA gene on the chromosomal DNA of RH 1810 was verified by PCR by the use of primers, the sequences of which are derived from the flanking regions of the gpsA gene. The following primers were used for the verification:

SEQ ID NO. 16: A_313    gaaggtgtgacgtctgcggatgaa

SEQ ID NO. 4: AR_180C   taatcccatagcaccaagcgcaaaccac

To examine the expression of the xyl gene of RH 1810, the xylanase activity was determined in the culture supernatant. The *Bacillus* strain in the shaking flask was grown on different media in two stages. In the first step the growing was carried out under selection pressure on minimum medium (Spizisen salt with 0.7%, glucose and 0.4% glutamine, water purified by the Millipore Water System, pH value at pH 7.2 before the sterilization). In the second step the complex medium was inoculated with 5% of the first culture. The medium corresponded to the following composition: 9% Glucidex 12, 2% corn steep powder, 1.32% $(NH_4)_2HPO_4$, 0.05% $MgSO_4*7H_2O$, 0.5% $CaCO_3$, tap water, adjustment of the pH value to pH 8.0 before the sterilization. The culture supernatants obtained after 48 hours of incubation were used to determine the xylanase activity according to the below method.

The xylane fragments released by the enzymatic cleavage of xylane were photometrically determined at 412 nm. 1 unit refers to the amount of enzymes that releases the equivalent of 1 μmol xylose by cleavage from xylane within one minute at 30° C. under standard conditions. The enzyme dilutions are prepared with 0.04 M sodium acetate buffer solution, pH 4.5. The reaction batch for the main value consists of 0.75 ml of a 0.5% oat spelt xylane solution in 0.04 M sodium acetate buffer, pH 4.5 and 0.25 ml of enzyme solution diluted correspondingly. As regards the blank value, 4 ml of a solution of 0.5% p-hydroxybenzoic acid hydrazide (PAHBAH, company Janssen Chimica), 0.465% Titriplex III (EDTA, company Merck) were added to 0.5 M NaOH before addition of the enzyme solution to stop the reaction.

After the incubation of 20 min at 30° C., the enzymatic reaction in the main value is stopped by addition of 4 ml of the same solution as for the blank value, and the color development is carried out by incubation at 75° C. for 30 min. The evaluation is conducted by calibration with a calibration curve in which xylose is used as standard.

As regards the double determination of the xylanase activities from culture supernatants of RH 1810, activities of 153.4 XylH $g^{-1}$ and 151.1 XylH $g^{-1}$ were measured. Thus, the antibiotic-resistance gene-free xylanase production showed in the shaking flask a higher productivity than production with RH 6000, in which kanamycin was used as selection pressure. By comparison the recombinant *Bacillus* strain RH 6000 (RH 1330::pIK91) obtained in the shaking flask a xylanase activity of only 57.8 XylH $g^{-1}$ (EP 0585617 B1).

Example 4

Determination of the Stability of the System

To determine the genetic stability of the gpsA-xyl-carrying plasmid in the GpsA⁻ *B. amyloliquefaciens* cells, the strain RH 1810 obtained according to Example 3 was examined in a shaking flask experiment without selection pressure in liquid medium. A preculture of RH 1810 was grown under selection pressure for this purpose, i.e., a medium in which the auxotrophic *B. amyloliquefaciens* cannot grow and in which neither glycerine nor G3P nor educts of glycerine or G3P are accessible for the *Bacillus* strain were used. The growing was carried out in a 150 ml Erlenmeyer shaking flask with 20 ml medium each time. The medium of the preculture consisted of the following composition; Spizizen salt+7% Glucidex 12–2% casein hydrolysate (pH value at pH 7.2). The first preculture was incubated for 16 h and herefrom the second preculture was inoculated with the same media composition. After 8-hour incubation, the main culture was inoculated herefrom. The growing without selection pressure was carried out in a 1 l Erlenmeyer shaking flask with 150 ml medium of, the composition each: 9% Glucidex 12, 2% corn steep powder, 1.32% $(NH_4)_2HPO_4$, 0.05% $MgSO_4*7H_2O$, 0.5% $CaCO_3$, tap water, adjustment of the pH valued to pH 8.0 before the sterilization. In this medium a growing of the GpsA⁻ *Bacillus* strain without the complementing plasmid pTP15 (Example 3: step 2) is possible. After 8 to 16 hours, the culture was each over-inoculated with 5% into two Erlenmeyer shaking flasks with fresh medium, whereby the one flask was used for the over-inoculation of the following flask and from the other flask the xylanase activity of the culture supernatant was determined after 24-hour incubation. It was cultivated for five days and nights; the main cultures were hereby over-inoculated four times. After each termination of the cultivation, the total cell number per ml medium was determined to be able to control the plasmid stability of pTP15 in RH 1810. The result is shown in Table 2.

TABLE 2

Plasmid stability in the pTP15-carrying transformants of GpsA⁻ *Bacillus amyloliquefaciens* cells RH 1626, verified on the basis of the xylanase activity by the generation number
RH 1810: *Bacillus amyloliquefaciens* Δ(gpsA)::pTP15

| accumulated duration of cultivation of the main culture [h] | number of over-inoculation of the main culture | generation number | relative xylanase activity [%] |
| --- | --- | --- | --- |
| 24 | 1 | 8 | 100 |
| 40 | 2 | 12 | 96 |
| 48 | 3 | 16 | 97 |
| 64 | 4 | 21 | 111 |
| 72 | 5 | 25 | 111 |

As shown in the result of Table 2, the xylanase activity without selection pressure remains stable over the 5-fold duration of a normal fermentation. This becomes apparent by the relative xylanase activity for the first culture without selection pressure remaining constant and even slightly increasing further.

Example 5

Production of Xylanase by Fermentation in a Bioreactor with the Recombinant System a) Preculture The strain RH 1810 was grown on selection plates (Spizizen salt with 0.7% glucose, 0.4% glutamine and 1% agar, water purified by the Millipore Water System, pH value at 7.2 before the sterilization). The incubation was carried out at 37° C. for at least 32 h.

1st preculture: A 1 l Erlenmeyer flask with baffle plates with 150 ml medium was inoculated with RH 1810 of the agar plate. The nutrient solution had the following composition:

| | |
|---|---|
| (NH$_4$)$_2$SO$_4$ | 2 g l$^{-1}$ |
| K$_2$HPO$_4$ | 14 g l$^{-1}$ |
| KH$_2$PO$_4$ | 6 g l$^{-1}$ |
| Na$_3$citrate × 2H$_2$O | 1 g l$^{-1}$ |
| MgSO$_4$ × 7H$_2$O | 0.2 g l$^{-1}$ |
| Glucidex 12 | 70 g l$^{-1}$ |
| casein hydrolysate | 20 g l$^{-1}$ | pH 7.2; sterilization 30 min 121° C.

The culture was incubated for 16 hours at 37° C. while shaking (150 rpm).

2nd preculture: 1 l Erlenmeyer flask with baffle plates was filled with 150 ml of the same composition and inoculated with 5% of the 1st preculture. The cultivation was carried out at 37° C. for 8 hours.

b) Bioreactor

Main culture: 20 l of a nutrient solution from

| | |
|---|---|
| Glucidex 12 | 90 g l$^{-1}$ |
| Corn steep powder | 20 g l$^{-1}$ |
| MgSO$_4$ × 7H$_2$O | 0.5 g l$^{-1}$ |
| CaCO$_3$ | 5 g l$^{-1}$ |
| (NH$_4$)$_2$HPO$_4$ | 13.2 g l$^{-1}$ | pH = 7.2; sterilization 30 min 121° C.

The bioreactor is inoculated with 5% of the 2nd preculture. Culture conditions: 37° C., ventilation 0.5 vvm, stirring with 450 rpm, 48 hours. The culture broth was cleared by centrifugation and used for the determination of xylanase activity. In the culture supernatant a xylanase activity of 166 XylH g$^{-1}$ was measured.

c) Baking Experiment

A dough was prepared from 100 parts by weight oat flour, 2 parts by weight salt, 3 parts by weight baking yeast, 58-60 parts by weight water and 40-50 ppm (based on dough weight) ascorbic acid in a dough kneader (fabricate Diosna) for 2-3 min on low level I and for 3-4 min on higher level II. Before the start of the kneading process, the respective amounts of enzymes were added to the water. The dough temperature was 25° C.-28° C. After a dough rest of 10 min, the dough was divided in 350 g dough pieces to produce German white bread ("freigeschobenes Weißbrot"). After a further dough rest of 20 min, the 350 g dough pieces were formed, refined for 70 min at 32° C. and 80% relative humidity, and baked for 32 min at 230° C.

After they were cooled down, the volume of the loaves was measured by means of a TexVol instrument BVM-L370 by laser scanning. The average value of all four loaves from one dough piece is considered in the evaluation.

Result of the Baking Experiments

The culture supernatant of a fermentation of RH 1810, which was carried out according to the conditions described in Examples 5a) and b), was used for the baking experiments. Loaves that were baked according to the explained procedure with the enzyme produced according to the invention showed the following properties:

TABLE 3

Concentration series with the baking-active xylanase of RH 1810 produced according to the invention compared to the xylanase produced by the recombinant *Bacillus* strain RH 6000 (EP 0585617 B1) The volume of the loaves to which the baking-active xylanase from RH 6000 was added is 100%.

| dosage UXyl per 100 kg flour | volume [%] |
|---|---|
| 1800 | 101 |
| 3600 | 102 |
| 5400 | 99 |

The invention claimed is:

1. An expression system for the production of one or more target polypeptide/target polypeptides, comprising a host cell in whose genome the DNA sequence that encodes glycerine-3-phosphate dehydrogenase is inactivated or partially or completely deleted and which is transformed by an extrachromosomal element that comprises a DNA sequence that encodes the target polypeptide(s) and glycerine-3-phosphate dehydrogenase, whereby not only the host cell genome but also the extrachromosomal element do not carry an antibiotic-resistance gene.

2. The expression system according to claim 1 wherein the extrachromosomal element is a plasmid, a phage, a phagemid or a transposon.

3. The expression system according to claim 1 wherein the extrachromosomal element comprises a DNA sequence that corresponds to the DNA sequence that encodes the endogenous glycerine-3-phosphate dehydrogenase of the host cell, a DNA sequence that encodes a related glycerine-3-phosphate dehydrogenase or a foreign glycerine-3-phosphate dehydrogenase.

4. The expression system according to claim 1 wherein the DNA sequence that encodes glycerine-3-phosphate dehydrogenase is under the control of a weak promoter.

5. The expression system according to claim 4 wherein the weak promoter is located upstream of the gpsA gene in FIG. 7 and is derived from plasmid pUB 110.

6. The expression system according to claim 4 wherein the weak promoter is the ptsH promoter from *B. subtilis*.

7. The expression system according to claim 1 wherein the host cell is derived from a Gram-positive bacterial cell.

8. The expression system according to claim 7 wherein the host cell is derived from a cell of the genus *Staphylococcus, Corynebacterium* or *Bacillus*.

9. The expression system according to claim 8 wherein the host cell is derived from *Bacillus amyloliquefaciens*.

10. The expression system according to claim 9 wherein the host cell is *Bacillus amyloliquefaciens* RH 1626 deposited under accession number DSM 18878.

11. The expression system according to claim 1 wherein the host cell is derived from a Gram-negative bacterial cell.

12. The expression system according to claim 1 wherein the target peptide is selected from the group consisting of hydrolytic enzymes, pectin-degrading enzymes, proteolytic enzymes and lipolytic enzymes.

13. The expression system according to claim 1 wherein the DNA sequence that encodes glycerine-3-phosphate dehydrogenase is selected from the group consisting of
 a) a nucleotide sequence according to SEQ ID NO: 1,
 b) a DNA sequence that encodes a protein sequence according to SEQ ID NO: 2,
 c) a DNA sequence that hybridizes under stringent conditions with a sequence according to a) or b),
 d) a DNA sequence that is related to the sequences according to a), b) or c) due to the degeneracy of the genetic code, and
 e) complementary strands to the sequences a) to d).

* * * * *

UNITED STATES PATENT AND TRADEMARK OFFICE
CERTIFICATE OF CORRECTION

| | | |
|---|---|---|
| PATENT NO. | : 8,465,946 B2 | Page 1 of 1 |
| APPLICATION NO. | : 12/598712 | |
| DATED | : June 18, 2013 | |
| INVENTOR(S) | : Céline Cadot et al. | |

It is certified that error appears in the above-identified patent and that said Letters Patent is hereby corrected as shown below:

On the Title page, first column, please replace the International Filing Date as follows:

from

(22) PCT Filed:   Feb. 12, 2008 to

(22) PCT Filed:   March 12, 2008

In the Specification:

At column 2, line number 24, replace "maker" with --marker--.

At column 5, line 9, replace "dart" with --darl.--.

At column 9, line 26, replace "Hilien" with --Hillen--.

At column 15, line 9, replace "by" with --bp--.

At column 15, line 29, replace "by" with --bp--.

At column 15, line 51, replace "pgsA" with --gpsA--.

At column 15, line 58, replace "pgsA" with --gpsA--.

At column 15, line 62, replace "Regions Flanking" with --regions flanking--.

At column 16, line 1, replace "pgsA" with --gpsA--.

At column 16, line 29, replace "pgsA" with --gpsA--.

At column 16, line 40, replace "Regions Flanking pgsA" with --regions flanking gpsA--.

At column 17, line 46, replace "by" with --bp--.

At column 18, line 44, replace "ligation, product" with --ligation product--.

Signed and Sealed this
Tenth Day of September, 2013

Teresa Stanek Rea
*Acting Director of the United States Patent and Trademark Office*

SEQUENCE LISTING

<160> NUMBER OF SEQ ID NOS: 18

<210> SEQ ID NO 1
<211> LENGTH: 3715
<212> TYPE: DNA
<213> ORGANISM: Bacillus amyloliquefaciens
<220> FEATURE:
<221> NAME/KEY: CDS
<222> LOCATION: (1338)..(2372)

<400> SEQUENCE: 1

```
aagggtacta tgggtaaacc tgtcgtagcc attgtcggaa gaccgaatgt gggaaaatcc      60
acaatcttta accggattgc gggtgaaaga atttcaatag tagaagatac ccccggagtg     120
acgcgggacc ggatatacag ttcggcggaa tggctgaatt atgattttaa cctgattgat     180
acgggcggaa ttgatatcgg agacgagccg tttctgacac agatccgcca gcaggctgaa     240
atcgccatgg acgaggctga tgtgatcatc tttatggtga acggccgcga aggtgtgacg     300
tctgcggatg aagaagtggc aaaaatactg taccggacga aaaaaccggt cgtattagcc     360
gttaataaat tagataatac cgaaatgaga gcgaacattt atgactttta tgcgctcggc     420
tttggagaac cgtatccgat ttcggggaca cacggtttag gattgggaga tttgctcgat     480
gcttgtgccg agcattttaa aaacattccg gagacgaagt acagtgatga tgtcgttcaa     540
ttctgcctga tcggccgccc gaatgtcgga aaatcatccc ttgtcaatgc gatgctcggc     600
```

```
gaagagcggg ttatcgtgag caacgtagcc ggaacgacta gagacgctgt ggatacggcg      660
ttcacttaca atcagcagga atttgtaatc gttgacacgg cgggaatgag aaaaaagggt      720
aaagtatatg aaacaacaga aaaatacagt gtgctgcggg cgttaaaagc cattgaccgc      780
tcagacgtcg tcggcgttgt gctgaatgca aagaaggca tccttgagca ggacaagcgg       840
atcgccggat acgcccatga agccgggaaa gccgtcgtca ttatcgtaaa caaatgggat      900
gccgttgata aggacgagcg cacgatgaaa gaatttgaac agaatattcg ggagcatttc      960
caatttctcg attatgcgcc ggtgctgttt atgtcggcac tgacgacaaa gcggattcat     1020
acactcatgc ctgcgattat taaagcgagt gaaaaccact ctctccgcgt gcagacaaat     1080
atcttaaatg atgtcatcat ggatgcggtc gccatgaatc cgactccgac gcacaacggc     1140
tcccgtctga aaatttatta tgcgactcaa gtcgctgtta agccgccgag cttcgttgtt     1200
tttgtcaacg atccggaact gatgcatttt tcttatgaac gcttttaga aaaccgaatc      1260 cgggacgctt tcggatttga aggtacgcca attaaaatat ttgcaagagc aagaaaataa     1320
aaaggtgtga tacagag atg aaa aaa gtg gca atg ctt gga gcg gga agc        1370
                    Met Lys Lys Val Ala Met Leu Gly Ala Gly Ser
                     1               5                  10 tgg ggc act gca ctt tct tta gtg ctg gct gat aac gga cat caa gtc       1418
Trp Gly Thr Ala Leu Ser Leu Val Leu Ala Asp Asn Gly His Gln Val
             15                  20                  25 atg atg tgg gga cac cgt gcc gaa ttg atc gat caa atc aac gaa ctg       1466
Met Met Trp Gly His Arg Ala Glu Leu Ile Asp Gln Ile Asn Glu Leu
         30                  35                  40 cat gaa aac aaa gat tac ctg ccg ggt gtg gag cta tca agt tct atc       1514
His Glu Asn Lys Asp Tyr Leu Pro Gly Val Glu Leu Ser Ser Ser Ile
     45                  50                  55 atc ggg aca gcc gat tta agc gag gct tta aaa gga gct gac ttc atc       1562
Ile Gly Thr Ala Asp Leu Ser Glu Ala Leu Lys Gly Ala Asp Phe Ile
 60                  65                  70                  75 att gtg gca gta ccg aca aaa gcc att cgg gaa gtg ctg aaa aag gct       1610
Ile Val Ala Val Pro Thr Lys Ala Ile Arg Glu Val Leu Lys Lys Ala
                 80                  85                  90 ctg ccg tac atc ccg aaa caa tcg att ttt gtt cat gtc agc aag gga       1658
Leu Pro Tyr Ile Pro Lys Gln Ser Ile Phe Val His Val Ser Lys Gly
             95                 100                 105 att gag ccg gat tcg ctt ctc cgc att tca gaa tta atg gag gag gag       1706
Ile Glu Pro Asp Ser Leu Leu Arg Ile Ser Glu Leu Met Glu Glu Glu
        110                 115                 120 ctg cct gag gag tac aga aaa gac atc gtc gtg ctt tca ggg ccg agc       1754
Leu Pro Glu Glu Tyr Arg Lys Asp Ile Val Val Leu Ser Gly Pro Ser
    125                 130                 135 cac gct gag gaa gtc gga tta aga cac ccg acg act gtt aca tca tct       1802
His Ala Glu Glu Val Gly Leu Arg His Pro Thr Thr Val Thr Ser Ser
140                 145                 150                 155 tca aaa aat atc aag gct gca gaa gcg gtt cag gat tta ttc atg aac       1850
Ser Lys Asn Ile Lys Ala Ala Glu Ala Val Gln Asp Leu Phe Met Asn
                160                 165                 170 cag cat ttc cgc gtc tat aca aat ccc gat atg atc ggt gtt gaa ata       1898
Gln His Phe Arg Val Tyr Thr Asn Pro Asp Met Ile Gly Val Glu Ile
            175                 180                 185 ggg gga gcg tta aaa aat atc atc gct ctt gca gcg ggg att aca gac       1946
Gly Gly Ala Leu Lys Asn Ile Ile Ala Leu Ala Ala Gly Ile Thr Asp
        190                 195                 200 gga ttg gga tac gga gat aat gca aaa gcg gcc tta atc acc cga ggt       1994
Gly Leu Gly Tyr Gly Asp Asn Ala Lys Ala Ala Leu Ile Thr Arg Gly
    205                 210                 215
```

```
ctt gct gaa atc gcc aga ctc ggc aca aag atg ggc gga aat ccg ctc    2042
Leu Ala Glu Ile Ala Arg Leu Gly Thr Lys Met Gly Gly Asn Pro Leu
220                 225                 230                 235 acc ttt tcc ggc ctg acc ggc gta ggc gat tta atc gtg acg tgt aca    2090
Thr Phe Ser Gly Leu Thr Gly Val Gly Asp Leu Ile Val Thr Cys Thr
            240                 245                 250 agc gtt cat tcc cga aac tgg cgc gcc ggc aac ctg ctc ggc aaa gga    2138
Ser Val His Ser Arg Asn Trp Arg Ala Gly Asn Leu Leu Gly Lys Gly
        255                 260                 265 tat aag ctg gaa gct gtc ctg gat aag atg ggg atg gtt gtt gaa ggc    2186
Tyr Lys Leu Glu Ala Val Leu Asp Lys Met Gly Met Val Val Glu Gly
    270                 275                 280 gtg cgg acg acg aaa gct gcg tat cag ctg tct caa aaa tat cag gtg    2234
Val Arg Thr Thr Lys Ala Ala Tyr Gln Leu Ser Gln Lys Tyr Gln Val
285                 290                 295 aaa atg ccg atc aca gaa gcg ctt cac caa gta tta ttt aat ggg cag    2282
Lys Met Pro Ile Thr Glu Ala Leu His Gln Val Leu Phe Asn Gly Gln
300                 305                 310                 315 aag gta gaa act gcc gta gaa tcc tta atg gcc aga gtg aaa acc cat    2330
Lys Val Glu Thr Ala Val Glu Ser Leu Met Ala Arg Val Lys Thr His
            320                 325                 330 gag atg gaa gac ttg gtc aac aca ttc gaa aac cgg gtg aag            2372
Glu Met Glu Asp Leu Val Asn Thr Phe Glu Asn Arg Val Lys
                335                 340                 345 tgacaataac atgccgtcag catattctga agtgacgaaa gtacaaaacg cagaactctc   2432
cggctgaaat cgcttaaaac atttgctgat ttaggcagaa gaggatgcag acgtacgcat   2492
ctacgcatac tatagcatcg aagtccaaga gagtgtatct cagacgtaca ggtgaatata   2552
gtcaacttga ctgaagcaaa gtcccccctct ttgcttcagt ttttttgttt tttcaataga   2612
tggaaaacct gttgatcttt tcaacatttg tatattaaaa tgaaatataa cgcttacaat   2672
gatgggacgg ggggcacgaa cgtgagtgtg gcattgatga aaatgtggtt tgcgcttggt   2732
gctatgggat taatgtttgt tgcggtcgcc tctatttatg tcagcaggta caaagtgaaa   2792
aacaaactga taaaagcagc ggtttcttca ctcgcttatg cctgcatggt catctcggga   2852
ttgatcgtgt taatggtcgt tttcagcggg cctgtcaatg aataaagcca aaaggggcg   2912 cggaatgcat aagttaaaaa tggccgtcat aacggcaatg gcggtgcttc tgctgtcggg   2972
ctgtctgtac cctgaagcaa aaaaaactga aaataaagta tcttacaaac atcagcttca   3032
gcaggtgcaa gcggcagtgg atgaattttaa aaaggcgaac ggcggacttc tgccgattca   3092
gacaaaagat atgaaaacac cgctctatca aaaatatccg atagatttta agcggctcgc   3152
gcccagatac atcgaggagc cgccggcctc agcttatgaa agcggaggaa tgtaccaata   3212
cgtgcttgtc gatgtggaaa ataagccgac cgtcaagctg gtcgatctcc aaatggcgga   3272
agcaatccgc gacatgaagc tgcgtgtcaa aatgtatcag gaaaagcata catatcctcc   3332
ctatgaggac gctgtttcaa aagggctgtt cactttaaat aaaaaaaagc tcggcatgaa   3392
agactctcct tcagtcaaaa gtccggtttc aggcacgtct ctgccgcttt taatcggcgc   3452
tgacggagaa atctatgccg actatcgcgt cgatctcgcc cgctgcctga aggaaaacaa   3512
aaagaaaatc aaaccggggg cggaaattca ggatatttta tggaaagaga ctcctttcgt   3572
cccggccttt tcagtcacat acaccgtaaa tgaaaaacag gaaccgtttt tttagaaag   3632 tcaaacgaaa caggaatgaa ccttttttccc gcgcatacaa ataggagaa aggtttttt   3692 gattttgata gaaaagactg cct                                          3715

<210> SEQ ID NO 2
```

-continued

```
<211> LENGTH: 345
<212> TYPE: PRT
<213> ORGANISM: Bacillus amyloliquefaciens

<400> SEQUENCE: 2

Met Lys Lys Val Ala Met Leu Gly Ala Gly Ser Trp Gly Thr Ala Leu
1               5                   10                  15

Ser Leu Val Leu Ala Asp Asn Gly His Gln Val Met Met Trp Gly His
                20                  25                  30

Arg Ala Glu Leu Ile Asp Gln Ile Asn Glu Leu His Glu Asn Lys Asp
            35                  40                  45

Tyr Leu Pro Gly Val Glu Leu Ser Ser Ile Ile Gly Thr Ala Asp
    50                  55                  60

Leu Ser Glu Ala Leu Lys Gly Ala Asp Phe Ile Ile Val Ala Val Pro
65                  70                  75                  80

Thr Lys Ala Ile Arg Glu Val Leu Lys Lys Ala Leu Pro Tyr Ile Pro
                85                  90                  95

Lys Gln Ser Ile Phe Val His Val Ser Lys Gly Ile Glu Pro Asp Ser
            100                 105                 110

Leu Leu Arg Ile Ser Glu Leu Met Glu Glu Leu Pro Glu Glu Tyr
        115                 120                 125

Arg Lys Asp Ile Val Val Leu Ser Gly Pro Ser His Ala Glu Glu Val
130                 135                 140

Gly Leu Arg His Pro Thr Thr Val Thr Ser Ser Ser Lys Asn Ile Lys
145                 150                 155                 160

Ala Ala Glu Ala Val Gln Asp Leu Phe Met Asn Gln His Phe Arg Val
                165                 170                 175

Tyr Thr Asn Pro Asp Met Ile Gly Val Glu Ile Gly Gly Ala Leu Lys
            180                 185                 190

Asn Ile Ile Ala Leu Ala Ala Gly Ile Thr Asp Gly Leu Gly Tyr Gly
        195                 200                 205

Asp Asn Ala Lys Ala Ala Leu Ile Thr Arg Gly Leu Ala Glu Ile Ala
    210                 215                 220

Arg Leu Gly Thr Lys Met Gly Gly Asn Pro Leu Thr Phe Ser Gly Leu
225                 230                 235                 240

Thr Gly Val Gly Asp Leu Ile Val Thr Cys Thr Ser Val His Ser Arg
                245                 250                 255

Asn Trp Arg Ala Gly Asn Leu Leu Gly Lys Gly Tyr Lys Leu Glu Ala
            260                 265                 270

Val Leu Asp Lys Met Gly Met Val Glu Gly Val Arg Thr Thr Lys
        275                 280                 285

Ala Ala Tyr Gln Leu Ser Gln Lys Tyr Gln Val Lys Met Pro Ile Thr
    290                 295                 300

Glu Ala Leu His Gln Val Leu Phe Asn Gly Lys Val Glu Thr Ala
305                 310                 315                 320

Val Glu Ser Leu Met Ala Arg Val Lys Thr His Glu Met Glu Asp Leu
                325                 330                 335

Val Asn Thr Phe Glu Asn Arg Val Lys
            340                 345

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
gctgttaagc cgccgagctt cgttg                                        25

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taatcccata gcaccaagcg caaaccac                                     28

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgacaaaagc cattcgggaa gtg                                          23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccgcgtcta tacaaatccc g                                            21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgtaggcgat ttaatcgtga c                                            21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatgaaagcg tctagattga aagg                                         24

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
catgtttgat tggtacctttt ttattttc                                    28
```

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
aagcgaaggt acccctcttt g                                            21
```

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
cctatttgaa tatgacatct ctagaaaatt tc                                32
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
cgaatccggc acgcttgtgg atttg                                        25
```

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
ccgtcccatc attgcatgcg ttatatttc                                    29
```

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gctaaaatct attattccgc ggttcagcaa tcgg                              34
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gtccattcac tatccgcggt ccctttttcag                                  30
```

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
gaaggtgtga cgtctgcgga tgaa                                              24

<210> SEQ ID NO 17
<211> LENGTH: 3734
<212> TYPE: DNA
<213> ORGANISM: Bacillus subtilis

<400> SEQUENCE: 17

| | | | | | |
|---|---|---|---|---|---|
| aagggtacta | tgggtaaacc | tgtcgtagcc | attgtcggga | gaccaaatgt | aggaaaatcc | 60
| acaatcttta | accggattgc | gggagaaaga | atttcaatag | tagaagatac | ccctggcgtg | 120
| acaagggatc | ggatatacag | ctcggctgaa | tggctgaatt | atgattttaa | tttgattgat | 180
| acggcggta | ttgatatcgg | tgatgagccg | tttttagcgc | agattcgcca | gcaagctgaa | 240
| atcgccatgg | atgaagcgga | cgtgattatt | tttatggtga | acggccgtga | aggcgtgaca | 300
| gctgctgatg | aagaagtggc | gaaaattttg | taccgcacaa | aaaagcctgt | tgttttagcg | 360
| gttaataaac | tggataacac | agaaatgaga | gcgaatattt | atgattttta | ttcgctaggc | 420
| tttggcgagc | cgtatccaat | tcgggaaca | cacggactcg | gactgggtga | tttactggat | 480
| gccgttgcag | agcattttaa | aaacattcct | gaaacgaaat | acaatgaaga | agttattcaa | 540
| ttctgtctga | tcggacgtcc | aaatgtcgga | agtcttcac | ttgtgaatgc | gatgctcggc | 600
| gaagaacgcg | ttattgtcag | caacgtggct | ggaacgacaa | gagatgctgt | tgatacgtca | 660
| tttacttaca | accagcagga | gtttgtcatt | gtcgatactg | caggtatgcg | aaaaaaaggg | 720
| aaagtctatg | aaacgactga | gaagtatagt | gtactgcggg | cgctaaaagc | gattgaccgc | 780
| tcagaagtcg | tggcggttgt | gctggatggc | gaagaaggca | ttattgaaca | ggacaagcgt | 840
| atcgccggtt | atgcacacga | agcgggcaag | gccgtcgtca | tcgtcgtaaa | caaatgggat | 900
| gctgttgaca | agatgagag | cacgatgaaa | gaatttgaag | aaaatattcg | cgatcatttt | 960
| caatttctgg | attatgcgcc | aatcctattt | atgtctgcct | taacgaaaaa | acggatccat | 1020
| actctgatgc | ctgcgattat | caaagctagt | gaaaatcatt | cacttcgagt | tcaaacaaac | 1080
| gtcttaaatg | atgtcatcat | ggacgctgtg | gcaatgaatc | cgacaccgac | tcataacggt | 1140
| tctcgtttga | aaatttacta | tgcgactcaa | gtgtcggtaa | agccgccaag | cttcgttgtg | 1200
| tttgtaaacg | atccggaact | gatgcatttt | tcatacgaac | ggttttttaga | aaaccgaatc | 1260
| agagacgcgt | tcggttttga | ggggacacca | atcaaaatat | ttgcaagagc | tagaaaataa | 1320
| aaaggtgtga | atcaaacatg | aaaaaagtca | caatgcttgg | agcggggagt | tggggaacag | 1380
| cactggcttt | agttctaact | gataatggaa | atgaagtgtg | tgtgtgggct | caccgtgcag | 1440
| atttaattca | tcaaattaat | gagttgcatg | aaaacaaaga | ttatttgccg | aatgttaagc | 1500
| tgtctacatc | cattaaagga | acaacagata | tgaaagaggc | tgtttcagac | gcagatgtca | 1560
| ttatcgttgc | ggtcccgaca | aaagcaattc | gggaagtgct | gagacaggct | gtccctttta | 1620
| taacgaaaaa | ggcagtcttt | gttcatgtca | gcaagggtat | tgagccagat | tcacttctgc | 1680
| gcatttctga | aattatggaa | attgagctcc | cgagtgatgt | cagaaaagat | atcgttgtcc | 1740

-continued

| | |
|---|---|
| tttccggccc gagtcatgcg gaagaagtag ggctgcggca ccccacaact gttactgcat | 1800 |
| cttcaaagag catgagggca gcagaagagg tgcaggatct atttattaat cacaattttc | 1860 |
| gggtgtacac aaatcctgac attatcggag ttgaaatcgg aggggcttta aaaatatta | 1920 |
| ttgcccttgc tgcaggaatt acagatggtt tagggtacgg tgacaatgcc aaagctgctt | 1980 |
| tgattacacg cggacttgcc gaaatcgcga gactcggaac gaaaatgggc ggaaatccct | 2040 |
| tgacgttctc tggattgaca ggagtaggcg atctgattgt gacgtgcaca agtgttcatt | 2100 |
| ccagaaactg gcgtgcgggc aatttgctcg gaaaagggta caagcttgaa gatgttcttg | 2160 |
| aagagatggg aatggtagtc gaaggcgtcc gcacgacgaa agcggcttat cagctttcga | 2220 |
| agaaatatga tgttaaaatg ccgattacag aagctctcca tcaggtccta ttcaacggac | 2280 |
| aaaaagtgga aaccgctgtt gaatctttaa tggcgagagg gaaaacccac gagatggagg | 2340 |
| atttggtaaa tacgtttgaa atcaagtga agtaaaagtg tcaatcaaat ggtgaatcgc | 2400 |
| atatcttaat tgaacgaaag cccgaaaaac agaagaacac ccaagtcttg ggatctcctg | 2460 |
| aaacattttg ccgatttagg caatagagga tgcatctgta tgccaagtcg catactatag | 2520 |
| catcgaagtc caagagagtg tttcttaaac gtgcaggtga atatagtcaa gttgactgaa | 2580 |
| gcgaaggtcc ccctctttgc ttcagttttt ttgttctatc aatggatgga aaatctggtt | 2640 |
| gatcttttcc ggcgctgtat attaaaatat aatataacgc ttatatctta catatcgggg | 2700 |
| aggcgcacgt cattgaatct ggcattgatg aaaatgtggt ttgctctagg gtccatgggt | 2760 |
| ctgatgtttc tggctgtagc ttccatctat ttaagccgct ttaagtgcca aaaccgtttt | 2820 |
| ttgaagattg cgatttcatc attcgcatac atgtgtatgc tcatatctgg aattattgtg | 2880 |
| tttgtcgtgg ttttttagcgg ccctgtcaat gaataaagct gtaaaaggaa gtgctgtatg | 2940 |
| ggtaaactga agtgcgcaat catttttgcg gcagtcgtgt tttatccgg atgtttatat | 3000 |
| ccaaatgaac ggaaaagcag tgtgcatgcc attccttatc aagaccagct aaagcaggtt | 3060 |
| caatctgctg ttgatgaatt tcaaaaggca aatggagggc tgcttcctat tcaaaccaaa | 3120 |
| gatatgtcga caccgctata tcaaaaatat ccgatagact ttaaccggtt agcgccaaga | 3180 |
| tacatagctg aacctccaag tacggcattt gaaagcgggg gagactatca atacgtgctt | 3240 |
| gttgacgtag agaacgatcc gactgttaaa ttaattgatc taaagatggc agaaaaaatt | 3300 |
| cgcgatgtga aattgcgcat ccaaatgtat cgtcaggagc atcaatatcc gccttacaag | 3360 |
| gatgtgctat ctcgtgattt atttacactc gatgagaaga agcttgggga tggcagctct | 3420 |
| cttacagtga caagcccaat ctcagggaat tccttgccgc ttatgattga cggagacgga | 3480 |
| gaaatatatg ccgattaccg gactgagctg gcttcttgcc tcaaaaaaag caaaaaaacg | 3540 |
| tttaaacccg ggactgaaat ccaggatatg atttggcatg aaacccccctt tgtcccgcg | 3600 |
| ttttctgtaa aatatacggt aaatgacaaa caggaacctg ttttttttaga aaatgatatg | 3660 |
| aaaaaggaat gaacctttct cccttgcata caaatagga gaaaggtttt tttatattaa | 3720 |
| tagattgagg atga | 3734 |

<210> SEQ ID NO 18
<211> LENGTH: 3741
<212> TYPE: DNA
<213> ORGANISM: Bacillus licheniformis

<400> SEQUENCE: 18

| | |
|---|---|
| aagggtacta tgggaaaacc tgtcgtagcc atagttggaa gacccaatgt ggggaagtcc | 60 |
| acgatcttta acaggatcgc gggcgaaaga atttcgattg tggaagatac acctggcgtg | 120 |

-continued

```
acgcgggatc ggatatacag ctctgccgag tggctgaatc acgacttcaa cctgattgat      180
acaggcggaa tcgaagtcgg cgatgagccg tttttggcgc agattcgcca tcaggccgag      240
atcgccatgg aagaagcaga tgtgattatt tcatgacga acggccgcga aggcgtcaca       300
gccgctgatg aagaagtggc aaaaatttta taccgtacaa aaaaaccgt cgttctggcg       360 gttaataaag tggataatcc tgaaatgaga gcaaacattt acgattttta tgccctcggc     420
tttggcgagc cgttcccgat tcagggacg catggccttg gtctcggcga tctgcttgac       480
gcggtcagcg aacattttaa aaacataccc gagacgaagt atgaggatga agtcgttcaa     540
ttttgcctca tcggccggcc gaacgtcgga aaatcctccc ttgtaaacgc catgattgga     600
gaagagcgcg ttatcgtcag caatattgcg ggaacgacgc gcgacgccat tgacacgagg     660
tttacataca atcaaagaga ctttgtcatc gtggatacag ccgggatgag aaaaaagggg     720
aaagtgtatg aggcaactga aaaatacagc gtcctccgag ctttaaaggc gatcgaccgt    780
tcagaagtcg tctgcgtcgt cttggacggc gaagaaggca ttattgagca ggacaagcgg    840
attgccggct atgcgcatga agcaggaaaa gctgttgtca tcgtcgtaaa caaatgggat    900
gcagtcgaaa aagacgagcg gacgatgaaa gaatttgaag aaaaggttag agaccacttt    960 caattttttgg actacgcgcc tgttttgttt atgtccgctt tgactaaaaa gcgcatccat  1020
acgctgatgc ctgcggtcat gacggcgagc gaaaaccatt cgatgagggt gcagaccaat  1080
attcttaatg atatcattat ggatgcggtg gctatgaacc cgacgccgac gcataatgga  1140
aaccggttaa aaatttatta tgcgacacaa gtggctgtga gccgccgac atttgtcgta    1200 tttgtcaatg accctgagct gatgcatttt tcttacgaac gcttttttgga aaaccggata  1260 cgcgacgcct tcggatttga aggaacacca atcaggattt tcgcaagagc aagaaaataa  1320
agaggtgtag taaaaatgac aaaagtatcg attttgggag ccggaagctg gggaacagcc  1380
ttggcgctcg ttttggcgga caaccagtac gatgtgtgca tatggggcca tcgtgaagaa  1440
ctgattcagc aaatcaatga acatcatgaa acaaagatt atctgccggg tgtcaaactt   1500
tctgaaaacg tgcgtgccac aacagatctt gaagctgcag tggctgatgt caagacgatc  1560
attgtcgccg ttccgacaaa agcgatccgc gaagttttgg cacaggctgt ttccttcatc   1620
aaccaaaagg cgattttgt acatgtttca aaaggaattg agcctgacac actgcttcga    1680
atttctgaaa tgatgaaaga agaaattccg gctgaattaa gggaggacat cgtcgttctg  1740
tccggaccga gccatgcgga agaagtcggt ttaaggcatc cgacgacagt aacggtatct  1800
gccgacagca gcattgaatc ggcccaggcg atccaggata tgtttatgaa ccagaatttc  1860
cgcgtgtata cgaatccgga tatgatcggc gtagagatcg gcggcgcgct gaaaaacgtc  1920
attgcgcttg ccgcgggcat tacagacggt ttgggatacg gagataatgc gaaagccgcg  1980
ctgattacaa ggggcttggc agaaatcgcc cggctcggca caaaaatggg cggaaatccg  2040
ctgacattct cgggtcttac tggaatcggg gacttgatcg tcacctgcac aagcgtccat  2100
tcacgaaatt ggcgagccgg taatatgctg ggtaaaggct tcaagctgga tgaagttctg  2160
gaagaaatgg ggatggtcgt cgaggggtgc cgcacgacaa aagccgctta tcagctttca  2220
aagaaatttg atgtaaaaat gccgatcacc gaagcactgc acaaagtatt gtttgacggc  2280 gaaaagttg agcggcagt cgaatcattg atggcaagag tcaaaacaca cgagatggaa    2340
gatcttgtga acacattcga aaatcaaatg aaatgaccgc cccatcatca actgcttta    2400 tactctcctc taagttcgtt ttaaaaaaac caaaacattt tggagactta ggcaagagag  2460 gatacattg tccgaagact tgcataaaat agaatcgaag tctggaagag ctgtatctta   2520
```

```
caaattgggt tatatagtca caatcattat gcctgaagca aagcccccct ctttgcttca    2580 ggctttttt tgcggctttt tccgtttcga aatattggaa aagctgttga acttctggtt    2640
tttcttatat aaaatgaaat ataacgctta catcacaaga aaaggtagaa ggagggcttc    2700
aatgtgaatg tcggtctgtt aaaaatgtgg tttgccttgg gatcaatggg cctgatgttc    2760
ttagcggtga ttgccatata cataagcaga tataaattta aaaaccgttt tttaaaaatt    2820
atcacgtcgt ttgtcgccta cacatgtatg ctcatctccg gcgtgatcgt cttttttgtc    2880
gtcttcagcg gccccgtcaa cgaataatgc ataaaaaagg aagattcata tgaaaatcgt    2940
aaacgttctg ctcgctattt tattgaccgc aatcatgtta agcggttgtt tgtaccctga    3000
agaaagaaag gcgaaaaaca gcgcaccgca tcagcaccag ctcaaagaag tgcaggcggc    3060
cgttgatgaa ttcagggagg cgacgggagg gcttctgccg attaagacaa gggatatggg    3120
cgtgccaatc tatcaaaaat accctatcga ttttaacagg ctgtccccc ggtatatggc     3180 tgagccgccg ggcacatcct atgaaaacgg cggagagtac ttgtacgttc ttgtcgatgt    3240
ggaaaaaaag ccgacggtca agctcattga tgtaaaaatg tcggaaatga tcagggagtt    3300
aaagcttcgg gtcgaaatgt ataaagatca gcacaagtat ccgccgtata aaaaagtcgt    3360
atccaagaac ttattcatgc ttgaccatga aaagctcgga ctgaaagagg cgccttctgt    3420
cacgagtccg ctttcgggca cctcgctgcc gcttctcgtc gatgaaaaag gcgacattaa    3480
agtggattac cggatggatt tggccaagct gatgaagaag tcgaaaaaaa cggtaaagcc    3540
gggcgaggaa gtccaagatt tgatgtggga agagacgcct ttcgttccgg cgttttcggt    3600
aaagtacaca gtgaatgaca aacaggaacc tgttttctc gaatagaata tcggtcaaaa     3660
tgcaagtatc agtcatgaac ctttctcctc ggcatacaat gaggagaaag gtttttcat     3720 gtatgccgaa aaaatttccc t                                              3741
```